US011141529B2

(12) United States Patent
Okiyama et al.

(10) Patent No.: US 11,141,529 B2
(45) Date of Patent: Oct. 12, 2021

(54) INFUSION APPARATUS

(71) Applicants: JMS CO., LTD., Hiroshima (JP);
Kyoto University, Kyoto (JP)

(72) Inventors: Tadashi Okiyama, Hiroshima (JP);
Hirofumi Nakagawa, Hiroshima (JP);
Masashi Kanai, Kyoto (JP); Yoko Hamabe, Kyoto (JP)

(73) Assignees: JMS CO., LTD., Hiroshima (JP);
Kyoto University, Kyoto (JP)

( * ) Notice: Subject to any disclaimer, the term of this patent is extended or adjusted under 35 U.S.C. 154(b) by 380 days.

(21) Appl. No.: 16/342,023

(22) PCT Filed: Oct. 11, 2017

(86) PCT No.: PCT/JP2017/036760
§ 371 (c)(1),
(2) Date: Apr. 15, 2019

(87) PCT Pub. No.: WO2018/074294
PCT Pub. Date: Apr. 26, 2018

(65) Prior Publication Data
US 2019/0247576 A1    Aug. 15, 2019

(30) Foreign Application Priority Data

Oct. 17, 2016 (JP) .............................. JP2016-203437

(51) Int. Cl.
*A61M 5/14* (2006.01)
*A61M 5/168* (2006.01)
(Continued)

(52) U.S. Cl.
CPC .......... *A61M 5/16813* (2013.01); *A61M 5/14* (2013.01); *A61M 5/1408* (2013.01);
(Continued)

(58) Field of Classification Search
CPC .. A61M 5/16813; A61M 5/172; A61M 5/168; A61M 5/14; A61M 5/1408;
(Continued)

(56) References Cited

U.S. PATENT DOCUMENTS 3,677,248 A  *  7/1972  McPhee .............. A61M 3/0241
                                                  604/500
4,946,439 A  *  8/1990  Eggers .............. A61M 5/16827
                                                  604/67

(Continued)

FOREIGN PATENT DOCUMENTS

JP     2-161955 A     6/1990
JP     2-286175 A    11/1990
(Continued)

OTHER PUBLICATIONS

International Search Report issued in PCT/JP2017/036760, dated Jan. 16, 2018 (2 pages).

*Primary Examiner* — Theodore J Stigell
*Assistant Examiner* — Daniel Moore
(74) *Attorney, Agent, or Firm* — Hamre, Schumann, Mueller & Larson, P.C.

(57) ABSTRACT

An infusion set (1) includes: a first flow path (10a) having a first connector (11a) and a downstream connector (19); a first open/close valve (12a), a first liquid surface sensor (13a), a second liquid surface sensor (13b), a drip chamber (14), and a variable valve (17) that are provided in this order on the first flow path from the first connector side toward the downstream connector side; a droplet sensor (15) with which the drip chamber is provided; a second flow path (10b) having a second connector (11b); and a second open/close valve (12b) provided on the second flow path. The second flow path is in communication with a portion of the first flow path between the first liquid surface sensor and the second liquid surface sensor. The controller is configured to (Continued)

control the first and second open/close valves and the variable valves based on signals from the first and second liquid surface sensors and the droplet sensor.

13 Claims, 6 Drawing Sheets

(51) Int. Cl.
*A61M 5/36* (2006.01)
*A61M 5/172* (2006.01)

(52) U.S. Cl.
CPC .......... *A61M 5/168* (2013.01); *A61M 5/1689* (2013.01); *A61M 5/172* (2013.01); *A61M 5/36* (2013.01)

(58) Field of Classification Search
CPC .... A61M 5/36; A61M 5/1689; A61M 5/1411; A61M 5/1407; A61M 5/1413; A61M 5/16822; A61M 5/16827; A61M 5/16877; A61M 5/16804; A61M 5/40
See application file for complete search history.

(56) References Cited

U.S. PATENT DOCUMENTS

| | | | |
|---|---|---|---|
| 5,968,014 A * | 10/1999 | Neftel | A61M 5/16827 604/151 |
| 6,468,251 B1 | 10/2002 | Yamanaka et al. | |
| 6,485,454 B1 * | 11/2002 | Yueh | A61M 5/1408 604/31 |
| 2011/0132482 A1 * | 6/2011 | Honma | A61M 5/385 137/605 |
| 2015/0247597 A1 | 9/2015 | Okiyama | |
| 2015/0265499 A1 | 9/2015 | Takeuchi | |
| 2018/0021512 A1 | 1/2018 | Fukuoka et al. | |

FOREIGN PATENT DOCUMENTS

| | | |
|---|---|---|
| JP | 7-236692 A | 9/1995 |
| JP | 11-197254 A | 7/1999 |
| JP | 11-511346 A | 10/1999 |
| JP | 2008-29607 A | 2/2008 |
| JP | 2013-252165 A | 12/2013 |
| JP | 2014-79355 A | 5/2014 |
| JP | 5774802 B1 | 9/2015 |
| WO | 2013/154050 A1 | 10/2013 |

* cited by examiner

INFUSION APPARATUS

TECHNICAL FIELD

The present invention relates to an infusion apparatus to be used to administer a liquid such as a medical solution via a patient's vein.

BACKGROUND ART

In the medical field, infusion to administer medicines, nutrients, electrolytes, or the like via a patient's vein is widely performed. For example, in the case of administering an anti-cancer agent, it is necessary to administer, to a patient, not only a medical solution that contains the anti-cancer agent but also a plurality of liquids, such as a premedication and a physiological saline for washing out flow paths. The plurality of liquids are stored separately in a plurality of respective infusion bags. An infusion set that includes a main line and a plurality of sub-injection lines is used to bring a plurality of infusion bags into communication with a needle that has been inserted into a patient's vein (e.g. see Patent Document 1).

Before infusion is started, an operation, which is called priming, to replace air that is within a flow path in the infusion set with a priming solution (e.g. a physiological saline) needs to be performed. After infusion has been started, the infusion bag needs to be sequentially switched to administer liquids in the plurality of infusion bags to a patient in a predetermined order. Also, since the flow rate of liquid differs depending on the type of liquid, the flow rate needs to be set appropriately every time the infusion bag is switched. These operations are usually performed manually by a nurse. From the start to end of infusion, a nurse is called by a nurse call system every time the liquid in each infusion bag runs out, placing a large work load on a nurse. Moreover, there is a possibility that a nurse will make an operation error of incorrectly setting the order in which infusion bags are to be switched or the flow rate. Such an operation error may lead to a critical medical accident.

Patent Document 2 describes an infusion pump that automatically switches between the plurality of infusion bags and sets the flow rate. However, in Patent Document 2, no consideration is given to priming.

PRIOR ART DOCUMENTS

Patent Document

[Patent Document 1] JP 5774802B
[Patent Document 2] JP 7-236692A
[Patent Document 3] WO 2013/154050
[Patent Document 4] JP 2014-079355A
[Patent Document 5] JP 11-197254A
[Patent Document 6] JP 2008-029607A
[Patent Document 7] JP 2013-252165A

DISCLOSURE OF INVENTION

Problem to be Solved by the Invention

The present invention aims to lighten the burden on an operator, reduce operation errors, and enables accurate and safe infusion by automating priming, switching between containers in which liquids are stored, and setting of the flow rate when administering a plurality of liquids to a patient.

Means for Solving Problem

A first infusion apparatus according to the present invention includes an infusion set and a controller. The infusion set includes: a first flow path having a first connector, which is to be connected to a first container for storing a first liquid, at one end, and a downstream connector at the other end; a first open/close valve, a first liquid surface sensor, a second liquid surface sensor, a drip chamber, and a variable valve that are provided in this order on the first flow path from the first connector side toward the downstream connector side; a droplet sensor that the drip chamber is provided with; a second flow path having a second connector, which is to be connected to a second container for storing a second liquid, at one end; and a second open/close valve provided on the second flow path. The second flow path is in communication with a portion of the first flow path between the first liquid surface sensor and the second liquid surface sensor. The controller is configured to control the first open/close valve, the variable valve, and the second open/close valve based on signals from the first liquid surface sensor, the second liquid surface sensor, and the droplet sensor.

A second infusion apparatus according to the present invention includes an infusion set and a controller. The infusion set includes: a first flow path having a first connector, which is to be connected to a first container for storing a first liquid, at one end, and a downstream connector at the other end; a first open/close valve, a drip chamber, and a variable valve that are provided in this order on the first flow path from the first connector side toward the downstream connector side; a droplet sensor, a first liquid surface sensor, and a second liquid surface sensor that the drip chamber is provided with in this order from an upper side toward a lower side; an air discharge tube that is in communication with a gas storing portion in the drip chamber; an air discharge tube open/close valve that the air discharge tube is provided with; a second flow path having a second connector, which is to be connected to a second container for storing a second liquid, at one end; and a second open/close valve provided on the second flow path. The second flow path is in communication with a portion of the first flow path between the first open/close valve and the drip chamber. The controller is configured to control the first open/close valve, the variable valve, the second open/close valve, and the air discharge tube open/close valve based on signals from the droplet sensor, the first liquid surface sensor, and the second liquid surface sensor.

Effects of the Invention

The first and second infusion apparatuses according to the present invention make it possible to automatically switch from the first container to the second container and set the flow rate of the first liquid and the second liquid, after a drip of the first liquid has been started. Also, the side-injection line (the second flow path) can be automatically primed immediately before a drip of the second liquid is given. Accordingly, the infusion apparatus according to the present invention is advantageous in lightening the work load on an operator. In addition, it is less likely that an operation error of incorrectly setting the order in which containers are to be switched or the flow rate occurs, and thus, the infusion apparatus according to the present invention is advantageous in increasing accuracy and safety of infusion.

Furthermore, according to the first infusion apparatus, air that was discharged from the side-injection line (the second flow path) as a result of priming the side-injection line does not leak out to the outside. This configuration is advantageous in preventing medicine exposure.

DESCRIPTION OF THE INVENTION

Figure 1:
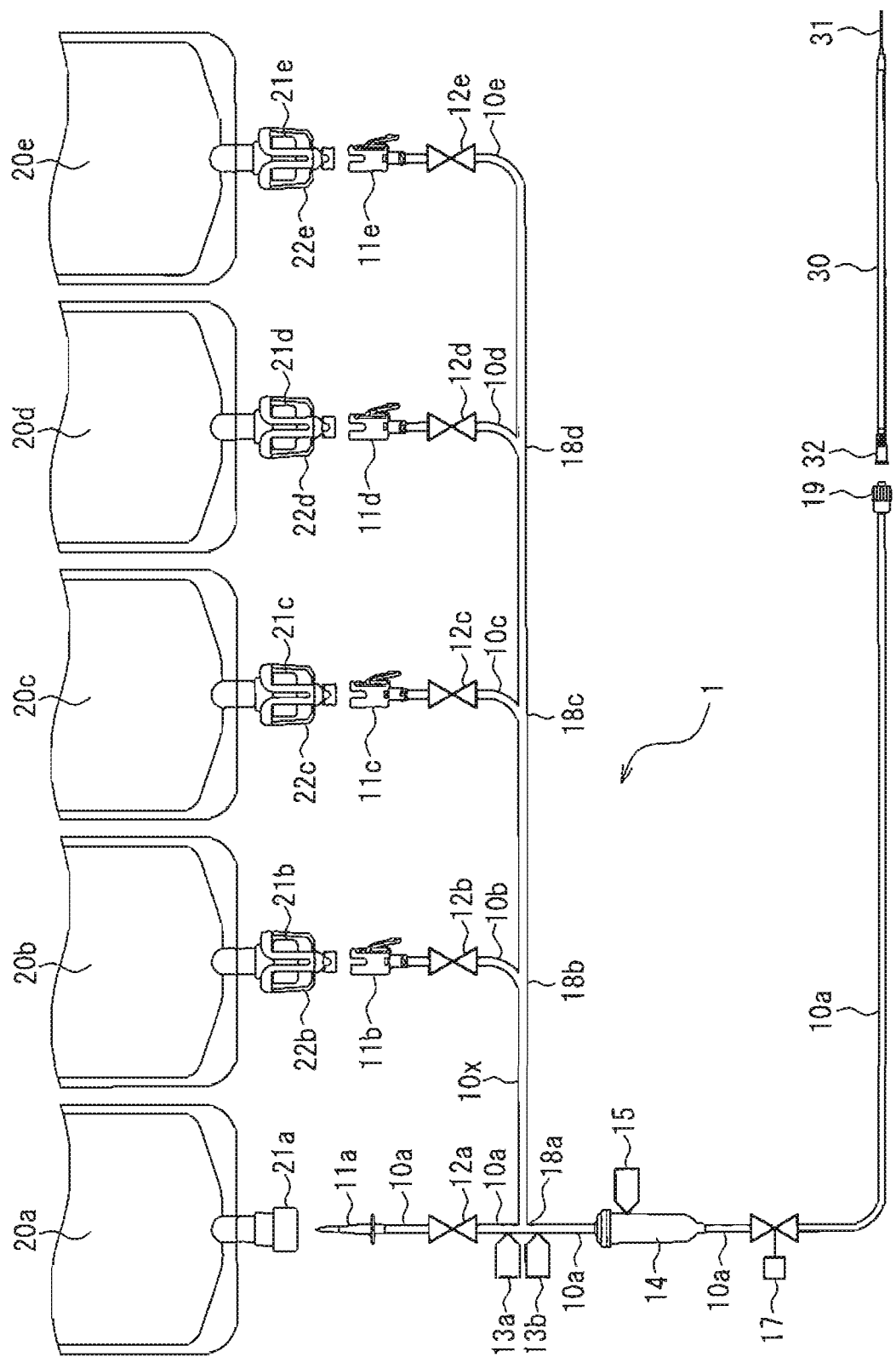
FIG. 1 shows an infusion set according to Embodiment 1 of the present invention.

In the above-described first infusion apparatus according to the present invention, if the second liquid surface sensor detects an interface between the first liquid and air, in a state where the second open/close valve is closed and the first open/close valve and the variable valve are opened to flow the first liquid from the first container toward the downstream connector, the variable valve may be closed and the second open/close valve may be opened to flow the second liquid into the second flow path, and if the first liquid surface sensor detects an interface between air and the second liquid, the first open/close valve may be closed and the variable valve may be opened to flow the second liquid from the second container toward the downstream connector. According to this configuration, termination of infusion of the first liquid, priming of the second flow path, and starting of infusion of the second liquid can be automatically performed sequentially.

In the above-described first infusion apparatus according to the present invention, the infusion set may further include: a third flow path having a third connector, which is to be connected to a third container for storing a third liquid, at one end; and a third open/close valve provided on the third flow path. In this case, the third flow path may be in communication with a portion of the first flow path between the first liquid surface sensor and the second liquid surface sensor. The controller may be configured to control the third open/close valve based on a signal from the second liquid surface sensor. With the first infusion apparatus that has the above configuration, in the case of further administering the third liquid in the third container, switching from the second container to the third container and setting of the flow rate of the third liquid can be automatically performed. Also, the third flow path can be automatically primed immediately before a drip of the third liquid is given. These configurations are advantageous in reducing the work load on an operator. In addition, air that was discharged from the third flow path as a result of priming the third flow path does not leak out to the outside. This configuration is advantageous in preventing medicine exposure.

In the above described first infusion apparatus according to the present invention, if the second liquid surface sensor detects an interface between the second liquid and air, in a state where the first open/close valve and the third open/close valve are closed and the second open/close valve and the variable valve are opened to flow the second liquid from the second container toward the downstream connector, the second open/close valve and the variable valve may be closed and the first open/close valve and the third open/close valve may be opened to flow the third liquid into the third flow path, and if the first liquid surface sensor detects an interface between air and the third liquid, the first open/close valve may be closed and the variable valve may be opened to flow the third liquid from the third container toward the downstream connector. According to the above configuration, termination of infusion of the second liquid, priming of the third flow path, and starting of infusion of the third liquid can be automatically performed sequentially.

The above-described first infusion apparatus according to the present invention may further include a sub-infusion set. the sub-infusion set may include: a first sub-flow path having a first sub-connector, which is to be connected to a first sub-container for storing a first sub-liquid, at one end, the other end being configured to be in communication with a portion of the first flow path on the downstream connector side of the variable valve, or with a flow path that is to be connected to the downstream connector in the infusion set; a first sub-open/close valve, a first sub-liquid surface sensor, a second sub-liquid surface sensor, a sub-drip chamber, and a sub-variable valve that are provided in this order on the first sub-flow path from the first sub-connector side toward the other end side of the first sub-flow path; a sub-droplet sensor that the sub-drip chamber is provided with; a second sub-flow path having a second sub-connector, which is to be connected to a second sub-container for storing a second sub-liquid, at one end; and a second sub-open/close valve provided on the second sub-flow path. The second sub-flow path may be in communication with a portion of the first sub-flow path between the first sub-liquid surface sensor and the second sub-liquid surface sensor. The controller may be configured to control the first sub-open/close valve, the sub-variable valve, and the second sub-open/close valve based on signals from the first sub-liquid surface sensor, the second sub-liquid surface sensor, and the sub-droplet sensor. According to the above configuration, drips of a plurality of liquids can be simultaneously given via a shared needle while independently controlling the flow rate of each liquid.

In the above-described first infusion apparatus according to the present invention, the variable valve in the infusion set and the sub-variable valve in the sub-infusion set may be configured to open simultaneously. According to this configuration, drips of a plurality of liquids can be started simultaneously, and thus, simultaneous drip of the plurality of liquids can be given reliably.

In the above-described second infusion apparatus according to the present invention, the air discharge tube may be in communication with a portion of the first flow path on the first connector side of the first open/close valve, or with the first connector. According to the above configuration, air that was discharged from the side-injection line (the second flow path) as a result of priming the side-injection line is collected into the first container, and does not leak out to the outside. This configuration is advantageous in preventing medicine exposure.

In the above-described second infusion apparatus according to the present invention, if the second liquid surface sensor detects that a liquid surface within the drip chamber has reached a lower limit position, in a state where the second open/close valve and the air discharge tube open/close valve are closed and the first open/close valve and the variable valve are opened to flow the first liquid from the first container toward the downstream connector, the first open/close valve and the variable valve may be closed and the second open/close valve and the air discharge tube open/close valve may be opened to flow the second liquid into the second flow path, and if the first liquid surface sensor detects that the liquid surface within the drip chamber has reached an upper limit position, the air discharge tube open/close valve may be closed and the variable valve may be opened to flow the second liquid from the second container toward the downstream connector. According to this configuration, termination of infusion of the first liquid, priming of the second flow path, and starting of infusion of the second liquid can be automatically performed sequentially.

In the above-described second infusion apparatus according to the present invention, the infusion set may further include: a third flow path having a third connector, which is to be connected to a third container for storing a third liquid, at one end; and a third open/close valve provided on the third flow path. In this case, the third flow path may be in communication with a portion of the first flow path between the first open/close valve and the drip chamber. The controller may be configured to control the third open/close valve based on a signal from the second liquid surface sensor. With the second infusion apparatus that has the above configuration, in the case of further administering the third liquid in the third container, switching from the second container to the third container and setting of the flow rate of the third liquid can be automatically performed. Also, the third flow path can be automatically primed immediately before a drip of the third liquid is given. These configurations are advantageous in reducing the work load on an operator.

In the above-described second infusion apparatus according to the present invention, if the second liquid surface sensor detects that a liquid surface within the drip chamber has reached a lower limit position, in a state where the first open/close valve, the third open/close valve, and the air discharge tube open/close valve are closed and the second open/close valve and the variable valve are opened to flow the second liquid from the second container toward the downstream connector, the second open/close valve and the variable valve may be closed and the third open/close valve and the air discharge tube open/close valve may be opened to flow the third liquid into the third flow path, and if the first liquid surface sensor detects that the liquid surface within the drip chamber has reached an upper limit position, the air discharge tube open/close valve may be closed and the variable valve may be opened to flow the third liquid from the third container toward the downstream connector. According to the above configuration, termination of infusion of the second liquid, priming of the third flow path, and starting of infusion of the third liquid can be automatically performed sequentially.

The above-described second infusion apparatus according to the present invention may further include a sub-infusion set. The sub-infusion set may include: a first sub-flow path having a first sub-connector, which is to be connected to a first sub-container for storing a first sub-liquid, at one end, the other end being configured to be in communication with a portion of the first flow path on the downstream connector side of the variable valve, or with a flow path that is to be connected to the downstream connector in the infusion set; a first sub-open/close valve, a sub-drip chamber, and a sub-variable valve that are provided in this order on the first sub-flow path from the first sub-connector side toward the other end side of the first sub-flow path; a sub-droplet sensor, a first sub-liquid surface sensor, and a second sub-liquid surface sensor that the sub-drip chamber is provided with in this order from an upper side toward a lower side; a sub-air discharge tube that is in communication with a gas storing portion in the sub-drip chamber; a sub-air discharge tube open/close valve that the sub-air discharge tube is provided with; a second sub-flow path having a second sub-connector, which is to be connected to a second sub-container for storing a second sub-liquid, at one end; and a second sub-open/close valve provided on the second sub-flow path. The second sub-flow path may be in communication with a portion of the first sub-flow path between the first sub-open/close valve and the sub-drip chamber. The controller may be configured to control the first sub-open/close valve, the sub-variable valve, the second sub-open/close valve, and the sub-air discharge tube open/close valve based on signals from the sub-droplet sensor, the first sub-liquid surface sensor, and the second sub-liquid surface sensor. According to the above configuration, drips of a plurality of liquids can be simultaneously given via a shared needle while independently controlling the flow rate of each liquid.

In the above-described second infusion apparatus according to the present invention, the variable valve in the infusion set and the sub-variable valve in the sub-infusion set may be configured to open simultaneously. According to this configuration, drips of a plurality of liquids can be started simultaneously, and thus, simultaneous drip of the plurality of liquids can be given reliably.

Hereinafter, the present invention will be described in detail while illustrating preferable embodiments. Needless to say, however, the present invention is not limited to the following embodiments. The drawings that are referenced in the following description show main members that constitute the embodiments of the present invention in a simplified manner for convenience of description. Accordingly, the present invention may include any member that is not shown in the following drawings. Also, members shown in the following drawings may be changed or omitted within the scope of the present invention. In the drawings referenced in the description of the embodiments, members that correspond to members that are shown in a drawing referenced in a preceding embodiment are assigned the same reference signs as those in the drawing illustrating the preceding embodiment. Redundant descriptions of such members are omitted, and description of the preceding embodiment should be considered where appropriate.

Embodiment 1

An infusion apparatus according to Embodiment 1 of the present invention includes an infusion set 1 and a controller. FIG. 1 shows a schematic configuration of the infusion set 1 (the controller is not shown). The infusion set 1 is used to sequentially administer, to a patient, a first liquid to a fifth liquid, which are stored respectively in a first container 20*a* to a fifth container 20*e*.

For example, the first liquid stored in the first container 20*a* may be a medical solution that contains a premedication, the second to fourth liquids stored in the second to fourth containers 20*b* to 20*d* may be medical solutions that contain an anti-cancer agent, and the fifth liquid stored in the fifth container 20*e* may be a physiological saline for washing out flow paths. The first container 20*a* to the fifth container 20*e* are sealed infusion bags, each of which is constituted by two soft sheets that are adhered to each other at their peripheral portions. The first container 20*a* to the fifth container 20*e* include ports 21*a* to 21*e*, respectively, for drawing out the stored liquids. Openings of the ports 21a to 21e are sealed by rubber plugs (which are not visible in FIG. 1).

The infusion set 1 includes a first flow path 10a, which serves as a main line. The first flow path 10a is constituted by a hollow, soft tube. The first flow path 10a has a first connector 11a and a downstream connector 19 at an upstream end and a downstream end thereof, respectively. The first connector 11a and the downstream connector 19 are in communication with each other via the first flow path 10a. The first connector 11a is a puncture needle (which may also be called a spike) that has an acute tip, and is inserted into the rubber plug provided in the port 21a of the first container 20a. The downstream connector 19 is connected to a connector 32, which is provided at an upstream end of a soft tube 30. A needle 31, which is to be inserted into a patient's vein, is provided at a downstream end of the tube 30.

A first open/close valve 12a, a first liquid surface sensor 13a, a second liquid surface sensor 13b, a drip chamber 14, and a variable valve 17 are provided in this order on the first flow path 10a from the first connector 11a side toward the downstream connector 19 side.

The first open/close valve 12a is an electric pinch clamp, for example, and opens and closes the first flow path 10a based on a signal from a controller (not shown). The first liquid surface sensor 13a and the second liquid surface sensor 13b detect an interface (i.e. liquid surface) between a liquid and air within the first flow path 10a, and output detection signals to the controller. The drip chamber 14 makes flowing of a liquid through the first flow path 10a visible. The drip chamber 14 is provided with a droplet sensor 15. The droplet sensor 15 detects droplets that drip down within the drip chamber 14, and outputs a detection signal to the controller. The variable valve 17 is an electric variable pinch clamp, for example, and adjusts the flow rate of a liquid flowing through the first flow path 10a by adjusting the cross-sectional area of the first flow path 10a based on a signal from the controller (not shown).

The infusion set 1 also includes a second flow path 10b, a third flow path 10c, a fourth flow path 10d, and a fifth flow path 10e, which serve as side-injection lines. The second to fifth flow paths 10b to 10e are constituted by hollow, soft tubes, similarly to the first flow path 10a. The second, third, fourth, and fifth flow paths 10b, 10c, 10d, and 10e have second, third, fourth, and fifth connectors 11b, 11c, 11d, and 11e, respectively, at their upstream ends. The second to fifth connectors 11b to 11e are lever lock connectors each including a male member and a lock lever with a claw (e.g. see Patent Document 3). The second to fifth connectors 11b to 11e are connected to the ports 21b to 21e of the second to fifth containers 20b to 20e via adapters 22b to 22e, respectively. Each of the adapters 22b to 22e includes a puncture needle, which has an acute tip capable of being inserted into a corresponding one of the rubber plugs in the ports 21b to 21e, an engaging claw, which is to engage with a corresponding one of the ports 21b to 21e, and a mixture injection port, which has an elastic partition member called a septum (e.g. see Patent Document 4). The male members of the second to fifth connectors 11b to 11e are inserted into the elastic partition members of the mixture injection ports, and the claws of the second to fifth connectors 11b to 11e engage with the mixture injection ports of the ports 21b to 21e. Connecting the second to fifth flow paths 10b to 10e to the ports 21b to 21e via the second to fifth connectors 11b to 11e and the adapters 22b to 22e is advantageous in reducing the likelihood of a hazardous medicine, such as an anti-cancer agent, leaking out to the outside and an operator being exposed to the medicine.

The second to fifth flow paths 10b to 10e are brought into communication with a portion of the first flow path 10a between the first liquid surface sensor 13a and the second liquid surface sensor 13b. In FIG. 1, one branch flow path 10x branches from a first branching portion 18a, which is provided on the first flow path 10a and has a T-shape (or a Y-shape), second, third, and fourth branching portions 18b, 18c, and 18d, which have a T-shape (or a Y-shape), are provided in this order on the branch flow path 10x, a second flow path 10b branches from the second branching portion 18b, a third flow path 10c branches from the third branching portion 18c, and a fourth flow path 10d and a fifth flow path 10e branch from the fourth branching portion 18d. In the present invention, the second to fifth flow paths (side-injection lines) 10b to 10e mean portions from the second to fifth connectors 11b, respectively, to 11e to the first flow path (main line) 10a. Accordingly, in the configuration in FIG. 1, each of the second to fifth flow paths 10b to 10e has a flow path portion that is shared with the other flow paths, and a unique flow path portion that is distinguished from the other flow paths.

Second, third, fourth, and fifth open/close valves 12b, 12c, 12d, and 12e are provided on the second, third, fourth, and fifth flow paths 10b, 10c, 10d, and 10e, respectively. If, as shown in FIG. 1, the second to fifth flow paths 10b to 10e have, as a portion thereof, a shared flow path portion shared by the other flow paths, the second to fifth open/close valves 12b to 12e are provided on the unique flow path portions that are distinguished from the other flow paths. The second to fifth open/close valves 12b to 12e are electric pinch clamps, for example, similarly to the first open/close valve 12a, and open and close the second to fifth flow paths 10b to 10e, respectively, based on a signal from the controller (not shown).

A description will now be given of a method of using the infusion apparatus according to Embodiment 1 that is configured as described above. Note that, in Embodiment 1, the first liquid to the fifth liquid flow within the infusion set 1 utilizing gravity, as will be described later, similarly to ordinary infusion.

The first container 20a to the fifth container 20e, in which the first liquid to the fifth liquid are stored, respectively, are suspended from, for example, an irrigator stand (not shown), with the ports 21b to 21e facing downward. The adapters 22b to 22e are attached to the ports 21b to 21e.

An infusion set 1 with the first to fifth open/close valves 12a to 12e and the variable valve 17 in a closed state is prepared. The first connector 11a in the infusion set 1 is connected to the port 21a of the first container 20a, and the second to fifth connectors 11b to 11e in the infusion set 1 are connected to the adapters 22b to 22e, respectively. The first flow path 10a is suspended in a substantially vertical direction due to gravity such that the first connector 11a, the first open/close valve 12a, the first liquid surface sensor 13a, the second liquid surface sensor 13b, the drip chamber 14, and the variable valve 17 are arranged in this order from the upper side toward the lower side. The second to fifth containers 20b to 20e are arranged at positions higher than the first open/close valve 12a. The downstream connector 19 is connected to the connector 32.

Initially, the first flow path 10a is primed using the first liquid (e.g. a premedication) in the first container 20a. That is to say, the first open/close valve 12a and the variable valve 17 are opened. The first liquid in the first container 20a flows from the first connector 11a into the first flow path 10a. When the first liquid reaches the tip of the needle 31 that is provided further downstream of the downstream connector 19, the first open/close valve 12a and/or the variable valve 17 are closed once. A flow path that extends from the first container 20a to the needle 31 through the first flow path 10a and the tube 31 is filled with the first liquid. The above operation to open and close the first open/close valve 12a and the variable valve 17 that accompanies the priming operation may be automatically performed by the controller, or may be manually performed by an operator.

Next, the needle 31 is inserted into a patient's vein.

Next, the controller again opens the first open/close valve 12a and the variable valve 17. A drip of the first liquid is started. The flow rate of the first liquid is monitored by the droplet sensor 15. The controller adjusts the degree of opening of the variable valve 17 such that the flow rate of the first liquid takes a predetermined value, based on a flow rate signal that is associated with the flow rate and is output from the droplet sensor 15.

Upon the first liquid in the first container 20a running out, air in the first container 20a flows out from the port 21a, following the first liquid. An interface (liquid surface) between the first liquid and air passes through the first connector 11a and moves down within the first flow path 10a. The second liquid surface sensor 13b, upon detecting the liquid surface, outputs a liquid surface detection signal to the controller. The controller closes the variable valve 17 based on the liquid surface detection signal from the second liquid surface sensor 13b. The drip of the first liquid is temporarily discontinued. A portion from the second liquid surface sensor 13b to the first container 20a is filled with air, and a portion on the downstream side (i.e. on the downstream connector 19 side) of the second liquid surface sensor 13b is filled with the first liquid.

The controller opens the second open/close valve 12b at the same time as or subsequently to closing the variable valve 17. The second liquid in the second container 20b flows into the second flow path 10b. Since the variable valve 17 and the third to fifth open/close valves 12c to 12e are closed, as a result of the second liquid flowing into the second flow path 10b, air that was in the second flow path 10b prior to the inflow of the second liquid flows into the first flow path 10a through the first branching portion 18a, and is pushed out toward the first container 20a. The interface (liquid surface) between air and the second liquid passes through the first branching portion 18a and moves up within the first flow path 10a. The first liquid surface sensor 13a, upon detecting the liquid surface, outputs a liquid surface detection signal to the controller. The controller closes the first open/close valve 12a and opens the variable valve 17, based on the liquid surface detection signal from the first liquid surface sensor 13a. Thereafter, the second liquid moves down the first flow path 10a through the first branching portion 18a, and flows toward the downstream connector 19. Thus, the drip of the first liquid remaining in the first flow path 10a is resumed, and subsequently, a drip of the second liquid is started. The flow rate of the second liquid is monitored by the droplet sensor 15. The controller adjusts the degree of opening of the variable valve 17 such that the flow rate of the second liquid takes a predetermined value, based on a flow rate signal that is associated with the flow rate and is output from the droplet sensor 15. Air that was in the second flow path 10b before the second open/close valve 12b was opened is confined to a portion of the first flow path 10a on the upstream side (i.e. on the first container 20a side) of the first open/close valve 12a and the first container 20a.

Upon the second liquid in the second container 20b running out, air in the second container 20b flows out from the port 21b, following the second liquid. The interface (liquid surface) between the second liquid and the air passes through the second connector 11b and moves within the second flow path 10b. The second liquid surface sensor 13b, upon detecting the liquid surface, outputs a liquid surface detection signal to the controller. The controller closes the second open/close valve 12b and the variable valve 17 based on the liquid surface detection signal from the second liquid surface sensor 13b. The drip of the second liquid is temporarily discontinued. A portion from the second liquid surface sensor 13b to the second container 20b is filled with air, and a portion on the downstream side (i.e. on the downstream connector 19 side) of the second liquid surface sensor 13b is filled with the second liquid.

The controller opens the first open/close valve 12a and the third open/close valve 12c at the same time as or subsequently to closing the second open/close valve 12b and the variable valve 17. The third liquid in the third container 20c flows into the third flow path 10c. Since the variable valve 17 and the second, fourth, and fifth open/close valves 12b, 12d, and 12e are closed, as a result of the third liquid flowing into the third flow path 10c, air that was in the third flow path 10c prior to the inflow of the third liquid flows into the first flow path 10a through the first branching portion 18a, and is pushed out toward the first container 20a. The interface (liquid surface) between the air and the third liquid passes through the first branching portion 18a and moves up within the first flow path 10a. The first liquid surface sensor 13a, upon detecting the liquid surface, outputs a liquid surface detection signal to the controller. The controller closes the first open/close valve 12a and opens the variable valve 17 based on this liquid surface detection signal from the first liquid surface sensor 13a. Thereafter, the third liquid moves down the first flow path 10a through the first branching portion 18a, and flows toward the downstream connector 19. Thus, the drip of the second liquid remaining in the first flow path 10a is resumed, and subsequently, a drip of the third liquid is started. The flow rate of the third liquid is monitored by the droplet sensor 15. The controller adjusts the degree of opening of the variable valve 17 such that the flow rate of the third liquid takes a predetermined value, based on a flow rate signal that is associated with the flow rate and is output from the droplet sensor 15. Air that was in the third flow path 10c before the third open/close valve 12c was opened is confined to a portion of the first flow path 10a on the upstream side (i.e. on the first container 20a side) of the first open/close valve 12a and the first container 20a.

Then, drips of the fourth liquid in the fourth container 20d and the fifth liquid in the fifth container 20e are sequentially given according to a similar procedure. If the droplet sensor 15 detects that the fifth liquid has run out, the controller closes the fifth open/close valve 12e and the variable valve 17. The drips of the first liquid to the fifth liquid thus end.

As described above, after starting a drip of the first liquid, the infusion apparatus according to Embodiment 1 automatically switches between the first container 20a to the fifth container 20e in which the first liquid to the fifth liquid are stored, respectively, and sets the flow rate of the first to the fifth liquids. This configuration is advantageous in lightening the work load on an operator and preventing a human error during operation.

The infusion apparatus according to Embodiment 1 automatically primes the second to fifth flow paths 10b to 10e after a drip of the first liquid has been started and immediately before drips of the second to fifth liquids are given, respectively. In the case of performing priming for an infusion set that includes one main line and a plurality of side-injection lines, such as the infusion set 1 according to Embodiment 1, a method called back-priming (which is also called priming-back), in which a priming solution is made to flow backward from the main line toward the side-injection lines, is often employed for the side-injection lines. This method needs to be manually performed by an operator, and requires laborious operations. According to Embodiment 1, the priming operation for the side-injection lines (the second to fifth flow paths 10b to 10e) can be automated. This point is also advantageous in lightening the work load on the operator.

In Embodiment 1, the side-injection lines (the second to fifth flow paths 10b to 10e) are primed using the respective liquids stored in the containers that are connected to the side-injection lines. If a hazardous medicine, such as an anti-cancer agent, is stored in a container connected to a side-injection line, there is a possibility that air that was discharged from the side-injection line due to priming contains vapor of the hazardous medicine. However, in Embodiment 1, air that was in the side-injection line before priming was performed is confined to the portion of the first flow path 10a on the upstream side (i.e. on the first container 20a side) of the first open/close valve 12a and the first container 20a, and does not leak out to the outside. This configuration is advantageous in reducing the likelihood of medicine exposure due to priming.

Embodiment 2

Figure 2:
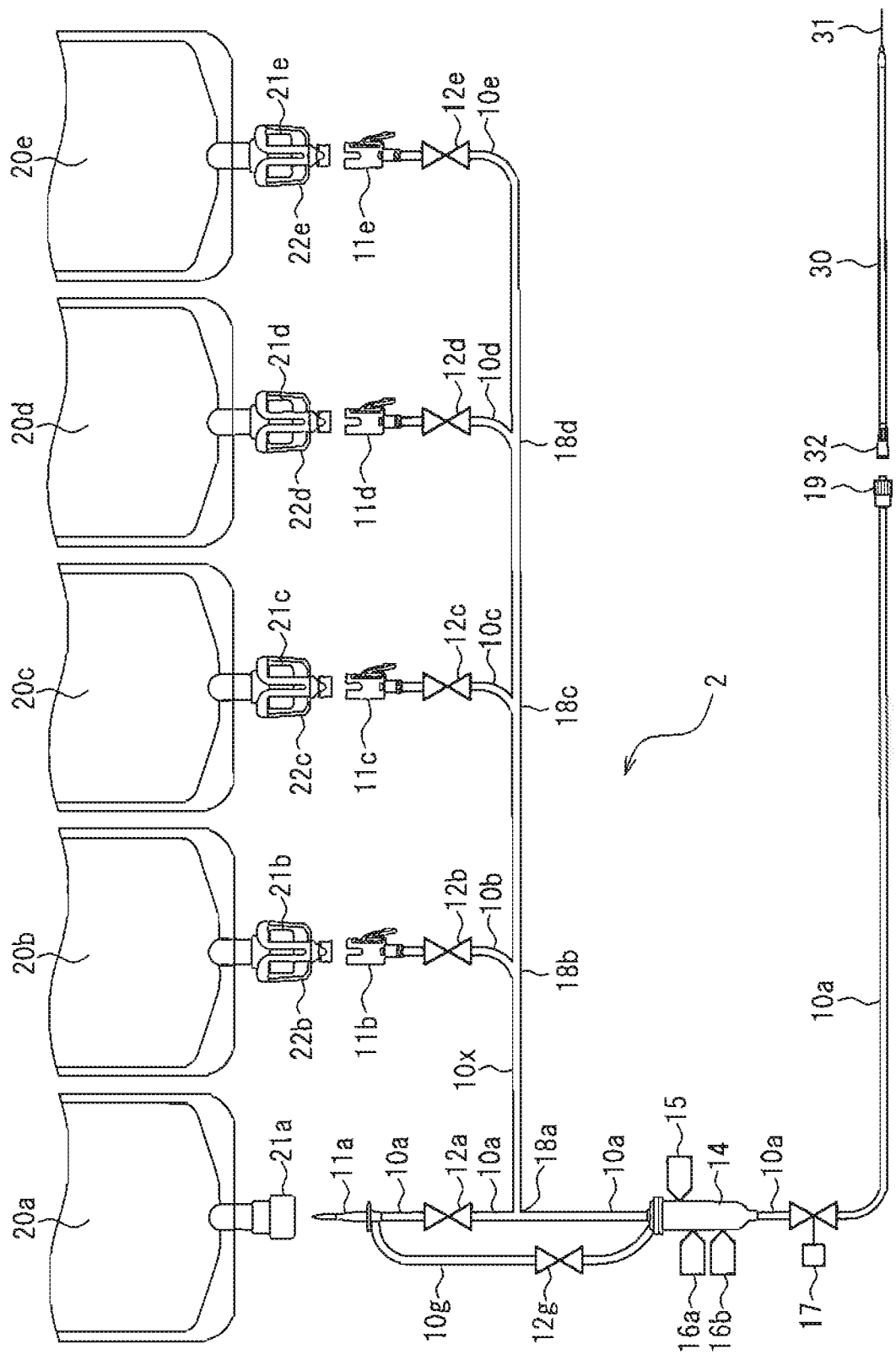
FIG. 2 shows an infusion set according to Embodiment 2 of the present invention.

An infusion apparatus according to Embodiment 2 of the present invention will be described, mainly regarding differences from Embodiment 1. The infusion apparatus according to Embodiment 2 includes an infusion set 2 and a controller. FIG. 2 shows a schematic configuration of the infusion set 2 (the controller is not shown). The infusion set 2 does not include the first liquid surface sensor 13a and the second liquid surface sensor 13b that are included in the infusion set 1 according to Embodiment 1. Instead, the drip chamber 14 is provided with a first liquid surface sensor 16a and a second liquid surface sensor 16b. Furthermore, the infusion set 2 includes an air discharge tube 10g, which bring a gas storing portion of the drip chamber 14 into communication with a portion of the first flow path 10a on the upstream side (i.e. on the first connector 11a side) of the first open/close valve 12a, or with the first connector 11a, and an air discharge tube open/close valve 12g, which is provided on the air discharge tube 10g.

The first liquid surface sensor 16a and the second liquid surface sensor 16b detect an interface (i.e. liquid surface) between a liquid in the drip chamber 14 and air, and output a detection signal to a controller (not shown). The droplet sensor 15, the first liquid surface sensor 16a, and the second liquid surface sensor 16b are arranged in this order on the drip chamber 14 from the upper side toward the lower side. The first liquid surface sensor 16a is provided so as to detect an upper limit position of the liquid surface within the drip chamber 14, and the second liquid surface sensor 16b is provided so as to detect a lower limit position of the liquid surface within the drip chamber 14.

The air discharge tube 10g is not limited, but may be constituted by a hollow, soft tube, similarly to the first to fifth flow paths 10a to 10e. The lower end of the air discharge tube 10g is in communication with a portion where air exists above the liquid surface within the drip chamber 14 (the gas storing portion). Ordinarily, the drip chamber 14 is constituted by a chamber in which a liquid is stored and that is transparent and has a cylindrical shape, and a cap for closing an opening at the upper end of the chamber. In Embodiment 2, the lower end of the air discharge tube 10g is connected to the cap. The lower end of the air discharge tube 10g may also be connected to the chamber as long as the air discharge tube 10g is in communication with the gas storing portion in the drip chamber 14. The air discharge tube 10g brings the gas storing portion in the drip chamber 14 into communication with a portion of the first flow path 10a on the upstream side (i.e. on the first container 20a side) of the first open/close valve 12a, when the first open/close valve 12a is closed. In Embodiment 2, the upper end of the air discharge tube 10g is connected to the base end of the first connector 11a, but may alternatively be connected to a portion of the first flow path 10a between the first open/close valve 12a and the first connector 11a.

The air discharge tube open/close valve 12g is an electric pinch clamp, for example, similarly to the first to fifth open/close valves 12a to 12e, and opens and closes the air discharge tube 10g based on a signal from the controller (not shown).

A description will now be given of a method of using the infusion apparatus according to Embodiment 2 that is configured as described above.

The first container 20a to the fifth container 20e, in which the first liquid to the fifth liquid are stored, respectively, are suspended from, for example, an irrigator stand (not shown), with the ports 21a to 21e facing downward. The adapters 22b to 22e are attached to the ports 21b to 21e.

An infusion set 2 with the first to fifth open/close valves 12a to 12e, the air discharge tube open/close valve 12g, and the variable valve 17 in a closed state is prepared. The first connector 11a in the infusion set 2 is connected to the port 21a of the first container 20a, and the second to fifth connectors 11b to 11e in the infusion set 2 are connected to the adapters 22b to 22e, respectively. The first flow path 10a is suspended in a substantially vertical direction due to gravity such that the first connector 11a, the first open/close valve 12a, the drip chamber 14, and the variable valve 17 are arranged in this order from the upper side toward the lower side. The second to fifth containers 20b to 20e are arranged at positions higher than the first open/close valve 12a. The downstream connector 19 is connected to the connector 32.

Initially, the first flow path 10a is primed using the first liquid (e.g. a premedication) in the first container 20a. That is to say, the first open/close valve 12a and the variable valve 17 are opened. The first liquid in the first container 10a flows from the first connector 20a into the first flow path 11a. When the first liquid reaches the tip of the needle 31 that is provided further downstream of the downstream connector 19, the first open/close valve 12a and/or the variable valve 17 are closed once. A flow path that extends from the first container 20a to the needle 31 through the first flow path 10a and the tube 31 is filled with the first liquid. The above operation to open and close the first open/close valve 12a and the variable valve 17 that accompanies the priming operation may be automatically performed by the controller, or may be manually performed by an operator.

Next, the needle 31 is inserted into a patient's vein.

Next, the controller again opens the first open/close valve 12a and the variable valve 17. A drip of the first liquid is started. The flow rate of the first liquid is monitored by the droplet sensor 15, and the liquid surface within the drip chamber 14 is monitored by the first liquid surface sensor 16a and the second liquid surface sensor 16b. The controller adjusts the degree of opening of the variable valve 17 such that the flow rate of the first liquid takes a predetermined value, based on a flow rate signal that is associated with the flow rate and is output from the droplet sensor 15. If the liquid surface within the drip chamber 14 is out of the range from the upper limit position (the first liquid surface sensor 16a) to the lower limit position (the second liquid surface sensor 16b), the controller may issue an alarm, or may also adjust the degree of opening of the variable valve 17 such that the liquid surface is located in this range.

Upon the first liquid in the first container 20a running out, air in the first container 20a flows out from the port 21a, following the first liquid. Droplets no longer drop down in the drip chamber 14, and the liquid surface is lowered. The droplet sensor 15, upon detecting the end of dripping, outputs a dripping-end signal to the controller. Subsequently, the second liquid surface sensor 16b, upon detecting that the liquid surface has reached the lower limit position, outputs a lowered liquid surface signal to the controller. The controller, upon receiving the lowered liquid surface signal subsequently to the dripping-end signal, closes the first open/close valve 12a and the variable valve 17. The drip of the first liquid is temporarily discontinued. A portion from the gas storing portion in the drip chamber 14 to the first container 20a is filled with air, and a portion on the downstream side (i.e. on the downstream connector 19 side) of the liquid surface within the drip chamber 14 is filled with the first liquid.

The controller opens the second open/close valve 12b and the air discharge tube open/close valve 12g at the same time as or subsequently to closing the first open/close valve 12a and the variable valve 17. The second liquid in the second container 20b flows into the second flow path 10b. Since the variable valve 17 and the first and third to fifth open/close valves 12a and 12c to 12e are closed, as a result of the second liquid flowing into the second flow path 10b, air that was in the second flow path 10b prior to the inflow of the second liquid flows into the first flow path 10a, the drip chamber 14, and the air discharge tube 10g, in this order, through the first branching portion 18a, and is pushed out toward the first container 20a. The second liquid that has flowed into the second flow path 10b flows into the drip chamber 14 through the first branching portion 18a and the first flow path 10a in this order. The liquid surface within the drip chamber 14 rises gradually. The first liquid surface sensor 16a, upon detecting that the liquid surface has reached the upper limit position, outputs a restored liquid surface signal to the controller. The controller closes the air discharge tube open/close valve 12g and opens the variable valve 17, based on the restored liquid surface signal from the first liquid surface sensor 16a. Thereafter, the second liquid moves down the first flow path 10a through the first branching portion 18a, and flows toward the downstream connector 19. Thus, the drip of the first liquid remaining in the first flow path 10a is resumed, and subsequently, a drip of the second liquid is started. The flow rate of the second liquid is monitored by the droplet sensor 15, and the liquid surface within the drip chamber 14 is monitored by the first liquid surface sensor 16a and the second liquid surface sensor 16b. The controller adjusts the degree of opening of the variable valve 17 such that the flow rate of the second liquid takes a predetermined value, based on a flow rate signal that is associated with the flow rate and is output from the droplet sensor 15. If the liquid surface within the drip chamber 14 is out of the range from the upper limit position (the first liquid surface sensor 16a) to the lower limit position (the second liquid surface sensor 16b), the controller may issue an alarm, or may adjust the degree of opening of the variable valve 17 such that the liquid surface is located in this range. Air that was in the second flow path 10b before the second open/close valve 12b was opened is confined to the gas storing portion in the drip chamber 14, the air discharge tube 10g, and the first container 20a.

Upon the second liquid in the second container 20b running out, air in the second container 20b flows out from the port 21b following the second liquid. Droplets no longer drop down in the drip chamber 14, and the liquid surface is lowered. The droplet sensor 15, upon detecting the end of dripping, outputs a dripping-end signal to the controller. Subsequently, the second liquid surface sensor 16b, upon detecting that the liquid surface has reached the lower limit position, outputs a lowered liquid surface signal to the controller. The controller, upon receiving the lowered liquid surface signal subsequently to the dripping-end signal, closes the second open/close valve 12b and the variable valve 17. The drip of the second liquid is temporarily discontinued. A portion from the gas storing portion in the drip chamber 14 to the second container 20b is filled with air, and a portion on the downstream side (i.e. on the downstream connector 19 side) of the liquid surface within the drip chamber 14 is filled with the second liquid.

The controller opens the third open/close valve 12c and the air discharge tube open/close valve 12g at the same time as or subsequently to closing the second open/close valve 12b and the variable valve 17. The third liquid in the third container 20c flows into the third flow path 10c. Since the variable valve 17 and the first, second, fourth, and fifth open/close valves 12a, 12b, 12d, and 12e are closed, as a result of the third liquid flowing into the third flow path 10c, air that was in the third flow path 10c prior to the inflow of the third liquid flows into the first flow path 10a, the drip chamber 14, and the air discharge tube 10g, in this order, through the first branching portion 18a, and is pushed out toward the first container 20a. The third liquid that has flowed into the third flow path 10c flows into the drip chamber 14 through the first branching portion 18a and the first flow path 10a in this order. The liquid surface within the drip chamber 14 rises gradually. The first liquid surface sensor 16a, upon detecting that the liquid surface has reached the upper limit position, outputs a restored liquid surface signal to the controller. The controller closes the air discharge tube open/close valve 12g and opens the variable valve 17, based on the restored liquid surface signal from the first liquid surface sensor 16a. Thereafter, the third liquid moves down the first flow path 10a through the first branching portion 18a, and flows toward the downstream connector 19. Thus, the drip of the second liquid remaining in the first flow path 10a is resumed, and subsequently, a drip of the third liquid is started. The flow rate of the third liquid is monitored by the droplet sensor 15, and the liquid surface within the drip chamber 14 is monitored by the first liquid surface sensor 16a and the second liquid surface sensor 16b. The controller adjusts the degree of opening of the variable valve 17 such that the flow rate of the third liquid takes a predetermined value, based on a flow rate signal that is associated with the flow rate and is output from the droplet sensor 15. If the liquid surface within the drip chamber 14 is out of the range from the upper limit position (the first liquid surface sensor 16a) to the lower limit position (the second liquid surface sensor 16b), the controller may issue an alarm, or may adjust the degree of opening of the variable valve 17 such that the liquid surface is located in this range. Air that was in the third flow path 10c before the third open/close valve 12c was opened is confined to the gas storing portion in the drip chamber 14, the air discharge tube 10g, and the first container 20a.

Thereafter, drips of the fourth liquid in the fourth container 20d and the fifth liquid in the fifth container 20e are sequentially given according to a similar procedure. If the droplet sensor 15 and the second liquid surface sensor 16b detect that the fifth liquid has run out, the controller closes the fifth open/close valve 12e and the variable valve 17. The drips of the first liquid to the fifth liquid thus end.

Similarly to Embodiment 1, in Embodiment 2 as well, after a drip of the first liquid has been started, switching between the first container 20a to the fifth container 20e in which the first liquid to the fifth liquid are stored, respectively, and setting of the flow rate of the first liquid to the fifth liquid are automatically performed. This configuration is advantageous in lightening the work load on an operator and preventing a human error in operation. The side-injection lines (the second to fifth flow paths 10b to 10e) are automatically primed after a drip of the first liquid has been started and immediately before drips of the second liquid to the fifth liquid are given, respectively. This configuration is also advantageous in reducing the work load on an operator.

Air that was in the side-injection lines (the second to fifth flow paths 10b to 10e) before the side-injection lines were primed is confined to the drip chamber 14, the air discharge tube 10g, and the first container 20a. As a result, the air does not leak out to the outside, similarly to Embodiment 1. This configuration is advantageous in reducing the likelihood of medicine exposure due to priming.

In the configuration in FIG. 2, the upper end of the air discharge tube 10g is connected to the first flow path 10a or the first connector 11a, but the present invention is not limited thereto. For example, the air discharge tube 10g may alternatively be connected to a sealed discharged air collection container (bag) that differs from the first to fifth containers 20a to 20e in which liquids are stored. In this case, air that was in the side-injection lines before priming is collected into the discharged air collection container, rather than the first container 10a.

In the case where liquids that pose no risk if a person is exposed thereto are stored in the first to fifth containers 20a to 20e, the upper end of the air discharge tube 10g may be open to the outside.

Embodiment 2 is the same as Embodiment 1, except for the above-described configuration. The descriptions of Embodiment 1 are also applied to Embodiment 2.

Embodiment 3

In the case of using the infusion apparatuses according to Embodiments 1 and 2 described above, the first liquid to the fifth liquid that are stored respectively in the first container 20a to the fifth container 20e are sequentially administered to a patient. At the actual medical site, however, there may be cases where a plurality of different liquids (e.g. two types of anti-cancer agents, or an anti-cancer agent and an enhancer for this anti-cancer agent) are to be simultaneously administered to a patient. Embodiment 3 of the present invention provides an infusion apparatus that enables such simultaneous administration of a plurality of liquids.

Figure 3:
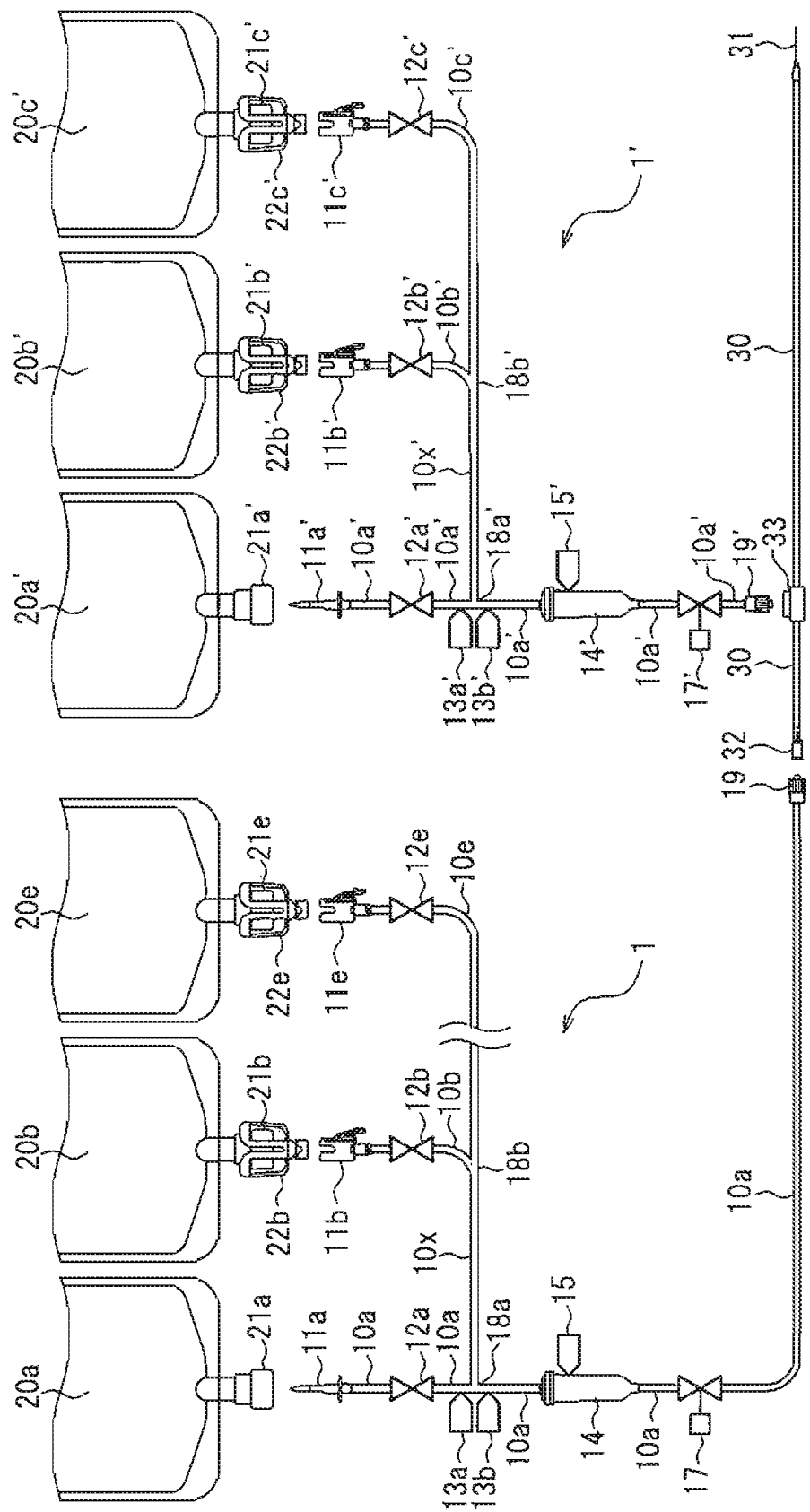
FIG. 3 shows an infusion set and a sub-infusion set according to Embodiment 3 of the present invention.

FIG. 3 shows a schematic configuration of the infusion apparatus according to Embodiment 3 (a controller is not shown). The infusion apparatus according to Embodiment 3 includes a sub-infusion set 1' in addition to the infusion set 1 described in Embodiment 1 (see FIG. 1), which serves as a main infusion set. The sub-infusion set 1' includes the same members as those constituting the infusion set 1, or members corresponding to the members that constitute the infusion set 1. To distinguish the members that constitute the sub-infusion set 1' from the corresponding members of the infusion set 1, sub- is appended to the names of the members that constitute the sub-infusion set 1', and ['] is appended to the reference numerals of these members. For example, "a first sub-connector 11a'" is a member that constitutes the sub-infusion set 1' and corresponds to "the first connector 11a" that constitutes the infusion set 1. Descriptions of the members that constitute the sub-infusion set 1' are omitted to avoid redundant descriptions. For the members with sub- and ['], descriptions of the members of the infusion set 1 that correspond to these members should be referenced as appropriate unless otherwise stated. Note that, in FIG. 3, the third container 20c and the fourth container 20d, and members that constitute the infusion set 1 and are associated with the third and fourth containers 20c and 20d are omitted to simplify the drawing.

First to third sub-liquids are stored in the first to third sub-containers 20a' to 20c', respectively. In Embodiment 3, the first sub-liquid stored in the first sub-container 20a' is a medical solution that contains a premedication. The second sub-liquid stored in the second sub-container 20b' is a medical solution that is to be administered simultaneously with the anti-cancer agent in the second container 20b and contains another anti-cancer agent. The third sub-liquid stored in the third sub-container 20c' is a physiological saline for washing out flow paths. However, these are examples, and the first to third sub-liquids may also be any other liquids.

The sub-infusion set 1' includes a first main line (a first sub-flow path 10a') and a plurality of side-injection lines, similarly to the infusion set 1. The sub-infusion set 1' differs from the infusion set 1 that includes four side-injection lines (the second to fifth flow paths 10b to 10e), in that the sub-infusion set 1' includes two side-injection lines (second and third sub-flow paths 10b' and 10c').

The first sub-flow path 10a' has a first sub-connector 11a' and a downstream sub-connector 19' at an upstream end and a downstream end thereof, respectively. The first sub-connector 11a' is a puncture needle (which is also called a spike) that has an acute tip, and is inserted into a rubber plug that is provided in a sub-port 21a' of the first sub-container 20a'. A first sub-open/close valve 12a', a first sub-liquid surface sensor 13a', a second sub-liquid surface sensor 13b', a sub-drip chamber 14', and a sub-variable valve 17' are provided on the first sub-flow path 10a' in this order from the first sub-connector 11a' side toward the downstream sub-connector 19' side. The sub-drip chamber 14' is provided with a sub-droplet sensor 15'.

The second sub-flow path 10b' and the third sub-flow path 10c' have a second sub-connector 11b' and a third sub-connector 11c', respectively, at their upstream ends. The second and third sub-connectors 11b' and 11c' are lever lock connectors (e.g. see Patent Document 3). The second and third sub-connectors 11b' and 11c' are connected to sub-ports 21b' and 21c' of the second and third sub-containers 20b' and 20c' via sub-adapters 22b' and 22c', respectively (e.g. see Patent Document 4). The second sub-flow path 10b' and the third sub-flow path 10c' are in communication with a portion of the first sub-flow path 10a' between the first sub-liquid surface sensor 13a' and the second sub-liquid surface sensor 13b'. One sub-branch flow path 10x' branches from a first sub-branching portion 18a', which is provided on the first sub-flow path 10a' and has a T'shape (or a Y-shape), a second sub-branching portion 18b', which has a T-shape (or a Y-shape), is provided on the sub-branch flow path 10x', and the second sub-flow path 10b' and the third sub-flow path 10c' branch from the second sub-branching portion 18b'. A second sub-open/close valve 12b' is provided at a portion of the second sub-flow path 10b' between the second sub-branching portion 18b' and the second sub-connector 11b'. A third sub-open/close valve 12c' is provided at a portion of the third sub-flow path 10c' between the second sub-branching portion 18b' and the third sub-connector 11c'.

Signals from the first and second sub-liquid surface sensors 13a' and 13b' and the sub-droplet sensor 15' are output to a controller (not shown), which is shared with the infusion set 1. The first to third sub-open/close valves 12a' to 12c' and the sub-variable valve 17' are controlled based on signals from the controller, which is shared with the infusion set 1.

A description will now be given of a method of using the infusion apparatus according to Embodiment 3 that is configured as described above.

The first container 20a to the fifth container 20e, in which the first liquid to the fifth liquid are stored, respectively, and the first sub-container 20a' to the third sub-container 20c', in which the first sub-liquid to the third sub-liquid are stored, respectively, are suspended from, for example, an irrigator stand (not shown), with the ports 21a to 21e and the sub-ports 21a' to 21c' facing downward. The adapters 22b to 22e and the sub-adapters 22b' and 22c' are attached to the ports 21b to 21e and the sub-ports 21b' and 21c', respectively.

An infusion set 1 with the first to fifth open/close valves 12a to 12e and the variable valve 17 in a closed state, and a sub-infusion set 1' with the first to third sub-open/close valves 12a' to 12c' and the sub-variable valve 17T in a closed state are prepared. Similarly to Embodiment 1, the first to fifth connectors 11a to 11e in the infusion set 1 are connected to the first to fifth containers 20a to 20e, and the downstream connector 19 in the infusion set 1 is connected to the connector 32. The first to third sub-connectors 11a' to 11c' in the sub-infusion set 1' are connected to the first to third sub-containers 20a' to 20c', and the downstream sub-connector 19' in the sub-infusion set 1' is connected to a mixture injection port 33 (e.g. see Patent Documents 5 and 6), which is provided on the tube 30. The first sub-flow path 10a' is suspended in a substantially vertical direction due to gravity such that the first sub-connector 11a', the first sub-open/close valve 12a', the first sub-liquid surface sensor 13a', the second sub-liquid surface sensor 13b', the sub-drip chamber 14', and the sub-variable valve 17 are arranged in this order from the upper side toward the lower side. The second and third sub-containers 20b' and 20c' are arranged at positions higher than the first sub-open/close valve 12a'.

Initially, the first flow path 10a and the first sub-flow path 10a' are primed. Either of the first flow path 10a and the first sub-flow path 10a' may be primed first. The case of priming the first sub-flow path 10a' first will be described. The first sub-open/close valve 12a' and the sub-variable valve 17' are opened. The first sub-liquid in the first sub-container 20a' flows from the first sub-connector 11a' into the first sub-flow path 10a'. When the first sub-liquid passes through the downstream sub-connector 19' and the mixture injection port 33 and flows into the tube 30, the first sub-open/close valve 12a' and/or the sub-variable valve 17 are closed. The first sub-flow path 10a' from the first sub-container 20a' to the downstream sub-connector 19' is filled with the first sub-liquid. Next, the first open/close valve 12a and the variable valve 17 are opened. The first liquid in the first container 20a flows from the first connector 11a into the first flow path 10a. When the first liquid flows past the downstream connector 19 and the mixture injection port 33 and reaches the tip of the needle 31, the first open/close valve 12a and/or the variable valve 17 are closed. A flow path that extends from the first container 20a to the needle 31 through the first flow path 10a and the tube 31 is filled with the first liquid. The above operation to open and close the valves 12a, 12a', 17, and 17' that accompanies the priming operation may be automatically performed by the controller, or may be manually performed by an operator.

Next, the needle 31 is inserted into a patient's vein.

Thereafter, drips of the first liquid to the fifth liquid are sequentially given, similarly to Embodiment 1. In Embodiment 3, however, the second sub-liquid in the second sub-container 20b' needs to be mixed with the second liquid in the second container 20b to give a drip thereof simultaneously with the second liquid. A drip of the first sub-liquid in the first sub-container 20a' needs to be given to the patient before the second sub-liquid. A drip of the third sub-liquid in the third sub-container 20c' needs to be given to the patient after the second sub-liquid. An example of a drip method according to Embodiment 3 will be described, mainly regarding the drips of the first to third sub-liquids.

Initially, the controller opens the first open/close valve 12a and the variable valve 17 to start giving a drip of the first liquid in the first container 20a. If the first liquid in the first container 20a runs out, and the second liquid surface sensor 13b detects an interface (liquid surface) between the first liquid and air, the controller closes the variable valve 17.

Next, the controller opens the first sub-open/close valve 12a' and the sub-variable valve 17' to start a drip of the first sub-liquid in the first sub-container 20a'. If the first sub-liquid in the first sub-container 20a' runs out, and the second sub-liquid surface sensor 13b' detects an interface (liquid surface) between the first sub-liquid and air, the controller closes the sub-variable valve 17'.

Next, the controller opens the second open/close valve 12b and the second sub-open/close valve 12b'. The second liquid in the second container 20b flows into the second flow path 10b, and the second sub-liquid in the second sub-container 20b' flows into the second sub-flow path 10b'.

As described in Embodiment 1, as a result of the second liquid flowing into the second flow path 10b, air that was in the second flow path 10b prior to the inflow of the second liquid is pushed out toward the first container 20a. The second liquid passes through the second flow path 10b and the first branching portion 18a, and flows toward the first container 20a. If the first liquid surface sensor 13a detects an interface (liquid surface) between the second liquid and air, the controller closes the first open/close valve 12a. The flow of the second liquid is temporarily stopped.

Similarly, as a result of the second sub-liquid flowing into the second sub-flow path 10b', air that was in the second sub-flow path 10b prior to the inflow of the second sub-liquid is pushed out toward the first sub-container 20a'. The second sub-liquid passes through the second sub-flow path 10b' and the first sub-branching portion 18a', and flows toward the first sub-container 20a'. If the first sub-liquid surface sensor 13a' detects an interface (liquid surface) between the second sub-liquid and air, the controller closes the first sub-open/close valve 12a'. The flow of the second sub-liquid is temporarily stopped.

After closing both the first open/close valve 12a and the first sub-open/close valve 12a', the controller simultaneously opens the variable valve 17 and the sub-variable valve 17'. The second liquid moves down the first flow path 10a through the first branching portion 18a, and flows toward the downstream connector 19. Similarly, the second sub-liquid moves down the first sub-flow path 10a' through the first sub-branching portion 18a', and flows toward the downstream sub-connector 19'. The second liquid and the second sub-liquid merge at the mixture injection port 33, and are administered to the patient through the needle 31. The flow rate of the second liquid is monitored by the droplet sensor 15, and is appropriately controlled by adjusting the degree of opening of the variable valve 17. Independently from the monitoring and control of the second liquid, the flow rate of the second sub-liquid is monitored by the sub-droplet sensor 15', and is appropriately controlled by adjusting the degree of opening of the sub-variable valve 17'.

If the second liquid in the second container 20a runs out, and the second liquid surface sensor 13b detects an interface (liquid surface) between the second liquid and air, the controller closes the second open/close valve 12b and the variable valve 17. Similarly, if the second sub-liquid in the second sub-container 20a' runs out, and the second sub-liquid surface sensor 13b' detects an interface (liquid surface) between the second sub-liquid and air, the controller closes the second sub-open/close valve 12b' and the variable valve 17'.

Next, the controller opens the first sub-open/close valve 12a' and the third sub-open/close valve 12c'. The third sub-liquid in the third sub-container 20c' flows into the third sub-flow path 10c', and air that was in the third sub-flow path 10c' prior to the inflow of the third sub-liquid is pushed out toward the first sub-container 20a'. The third sub-liquid passes through the third sub-flow path 10c' and the first sub-branching portion 18a', and flows toward the first sub-container 20a'. If the first sub-liquid surface sensor 13a' detects an interface (liquid surface) between the third sub-liquid and air, the controller closes the first sub-open/close valve 12a'. The flow of the third sub-liquid is temporarily stopped.

Next, the controller opens the sub-variable valve 17'. The third liquid moves down the first sub-flow path 10a' through the first sub-branching portion 18a', and flows toward the downstream sub-connector 19'. Thus, the drip of the second sub-liquid remaining in the first sub-flow path 10a' is resumed, and subsequently, a drip of the third sub-liquid is started. The flow rate of the third sub-liquid is monitored by the sub-droplet sensor 15', and is appropriately controlled by adjusting the degree of opening of the sub-variable valve 17'.

If the sub-droplet sensor 15' detects that the third sub-liquid has run out, the controller closes the third sub-open/close valve 12c' and the sub-variable valve 17'.

Thereafter, drips of the third liquid to the fifth liquid are sequentially given, similarly to Embodiment 1.

As described above, with the infusion apparatus according to Embodiment 3, two different liquids can be mixed, and a drip of the mixed liquid can be given to a patient. With the infusion apparatus (see FIG. 1) according to Embodiment 1 as well, the second liquid and the third liquid can be mixed and a drip of the mixed liquid can be given by simultaneously opening the second and third open/close valves 12b and 12c, for example. In this case, however, the flow rate of the second liquid and the third liquid cannot be separately monitored and independently controlled. According to Embodiment 3, drips of two different liquids can be simultaneously given, while separately monitoring and independently controlling the flow rates of the two liquids. Accordingly, for example, drips of two liquids, such as two different anti-cancer agents, or an anti-cancer agent and an enhancer for this anti-cancer agent, can be simultaneously given via the shared needle 31 while appropriately controlling the flow rates of the respective liquids.

The sub-infusion set 1' has the same basic configuration as that of the infusion set 1. Therefore, the sub-infusion set 1' exhibits the following effects, which are similar to those of Embodiment 1.

After a drip of the first sub-liquid has been started, switching between the first sub-containers 20a' to the third sub-container 20c' in which the first sub-liquid to the third sub-liquid are stored, and setting of the flow rate of the first sub-liquid to the third sub-liquid are automatically performed. This configuration is advantageous in lightening the work load on an operator and preventing a human error in operation.

The side-injection lines (the second sub-flow path 10b' and the third sub-flow path 10c') are automatically primed after a drip of the first sub-liquid has been started and immediately before drips of the second sub-liquid and third sub-liquid are given, respectively. This configuration is also advantageous in reducing the work load on an operator.

Air that was in the side-injection lines (the second sub-flow path 10b' and the third sub-flow path 10c') before the side-injection lines were primed does not leak out to the outside due to the priming. This configuration is advantageous in reducing the likelihood of medicine exposure due to priming in the case where a hazardous medical solution, such as an anti-cancer agent, is stored in a container that is connected to a side-injection line.

Embodiment 3 is the same as Embodiment 1, except for the above-described configuration. The descriptions of Embodiment 1 are also applied to Embodiment 3.

Embodiment 4

Embodiment 4 of the present invention also provides an infusion apparatus that enables simultaneous administration of a plurality of liquids, similarly to Embodiment 3.

Figure 4:
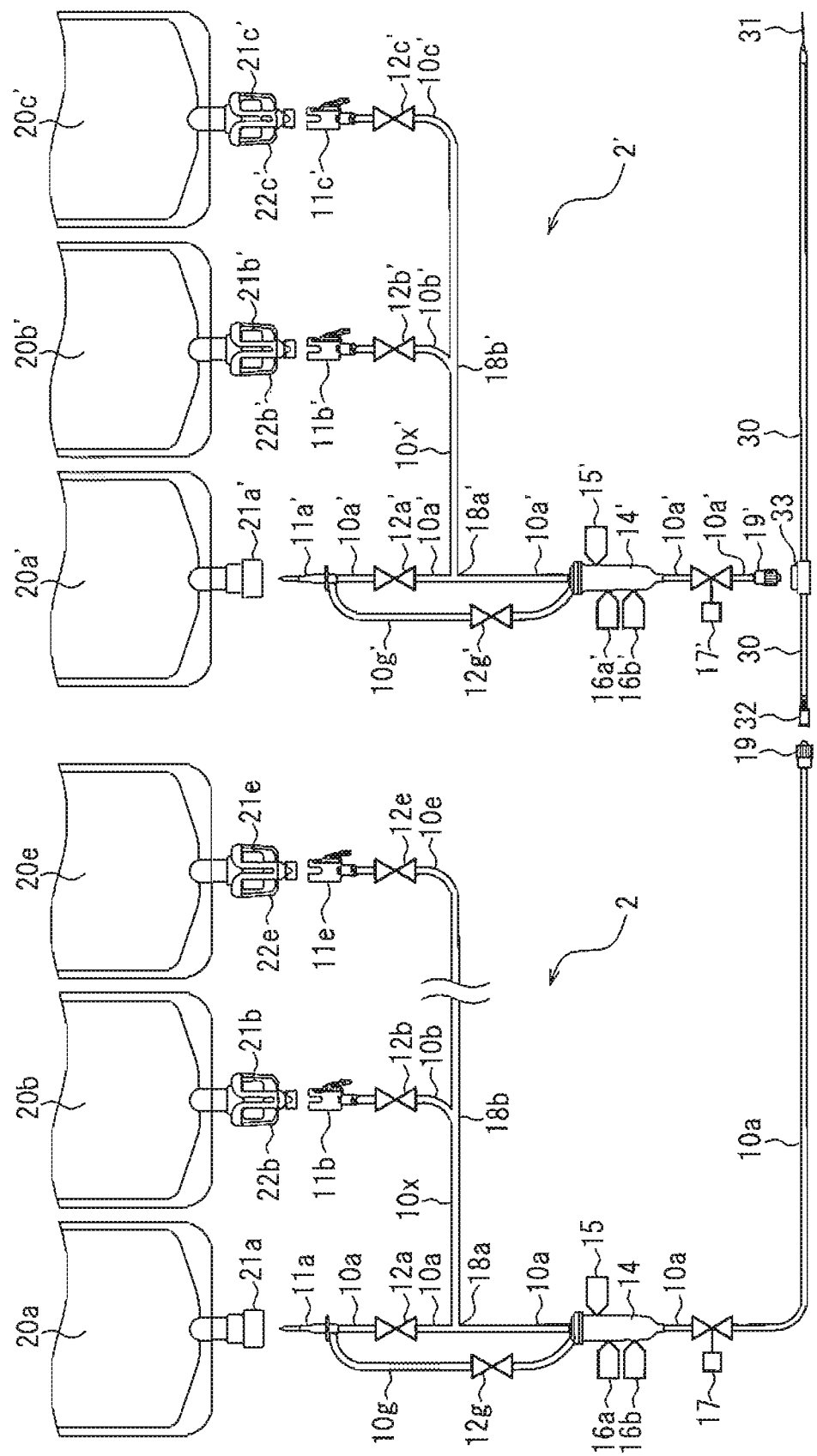
FIG. 4 shows an infusion set and a sub-infusion set according to Embodiment 4 of the present invention.

FIG. 4 shows a schematic configuration of an infusion apparatus according to Embodiment 4 (the controller is not shown). The infusion apparatus according to Embodiment 4 includes a sub-infusion set 2' in addition to the infusion set 2 described in Embodiment 2 (see FIG. 2), which serves as a main infusion set. The sub-infusion set 2' includes the same members as those constituting the infusion set 2, or members corresponding to the members that constitute the infusion set 2. Ib distinguish the members that constitute the sub-infusion set 2' from the corresponding members of the infusion set 2, sub- is appended to the names of the members that constitute the sub-infusion set 2', and ['] is appended to the reference numerals of these members. Descriptions of the members that constitute the sub-infusion set 2' will be omitted to avoid redundant descriptions. For the members with sub- and ['], descriptions of the members of the infusion set 2 that correspond to these members should be referenced as appropriate unless otherwise stated. Note that, in FIG. 4, the third container 20c and the fourth container 20d, and the members that constitute the infusion set 2 and are associated with the third and fourth containers 20c and 20d are omitted to simplify the drawing.

First to third sub-liquids are stored in the first to third sub-containers 20a' to 20c', respectively. Similarly to Embodiment 3, in Embodiment 4, the first sub-liquid stored in the first sub-container 20a' is a medical solution that contains a premedication. The second sub-liquid stored in the second sub-container 20b' is a medical solution that is to be administered simultaneously with the anti-cancer agent in the second container 20b and contains another anti-cancer agent. The third sub-liquid stored in the third sub-container 20c' is a physiological saline for washing out flow paths. However, these are examples, and the first to third sub-liquids may also be any other liquids.

Similarly to the infusion set 2, a sub-drip chamber 14' is provided with a sub-droplet sensor 15', a first sub-liquid surface sensor 16a', and a second sub-liquid surface sensor 16b' in this order from the upper side toward the lower side. A sub-air discharge tube 10g' brings a gas storing portion in the sub-drip chamber 14' into communication with a portion of the first sub-flow path 10a' on the upstream side (i.e. on the first sub-connector 11a' side) of a first sub-open/close valve 12a', or with the first sub-connector 11a'. A sub-air discharge tube open/close valve 12g' is provided on the sub-air discharge tube 10g'.

Signals from the first and second sub-liquid surface sensors 16a' and 16b' and the sub-droplet sensor 15' are output to a controller (not shown), which is shared with the infusion set 2. The first to third sub-open/close valves 12a' to 12c', the sub-variable valve 17', and the sub-air discharge tube open/close valve 12g' are controlled based on signals from the controller, which is shared with the infusion set 2.

A description will now be given of a method of using the infusion apparatus according to Embodiment 4 that is configured as described above.

The first container 20a to the fifth container 20e in which the first liquid to the fifth liquid are stored, respectively, and the first sub-container 20a' to the third sub-container 20c' in which the first sub-liquid to the third sub-liquid are stored, respectively, are suspended from, for example, an irrigator stand (not shown), with the ports 21a to 21e and sub-ports 21a' to 21c' facing downward. The adapters 22b to 22e and sub-adapters 22b' and 22c' are attached to the ports 21b to 21e and the sub-ports 21b' and 21c', respectively.

An infusion set 2 with the first to fifth open/close valves 12a to 12e, the air discharge tube open/close valve 12g, and the variable valve 17 in a closed state, and a sub-infusion set 2' with the first to third sub-open/close valves 12a' to 12c', the sub-air discharge tube open/close valve 12g', and the sub-variable valve 17' in a closed state, are prepared. Similarly to Embodiment 2, the first to fifth connectors 11a to 11e in the infusion set 2 are connected to the first to fifth containers 20a to 20e, respectively, and the downstream connector 19 in the infusion set 2 is connected to the connector 32. The first to third sub-connectors 11a' to 11c' in the sub-infusion set 2' are connected to the first to third sub-containers 20a' to 20c', and the downstream sub-connector 19' in the sub-infusion set 2' is connected to a mixture injection port 33 (e.g. see Patent Documents 5 and 6), which is provided on the tube 30. The first sub-flow path 10a' is suspended in a substantially vertical direction due to gravity such that the first sub-connector 11a', the first sub-open/close valve 12a', the sub-drip chamber 14', and the sub-variable valve 17' are arranged in this order from the upper side toward the lower side. The second and third sub-containers 20b' and 20c' are arranged at positions higher than the first sub-open/close valve 12a'.

Initially, the first flow path 10a and the first sub-flow path 10a' are primed. Either of the first flow path 10a and the first sub-flow path 10a' may be primed first. The case of priming the first sub-flow path 10a' first will be described. The first sub-open/close valve 12a' and the sub-variable valve 17' are opened. The first sub-liquid in the first sub-container 20a' flows from the first sub-connector 11a' into the first sub-flow path 10a'. When the first sub-liquid passes through the downstream sub-connector 19' and the mixture injection port 33 and flows into the tube 30, the first sub-open/close valve 12a' and/or the sub-variable valve 17 are closed. The first sub-flow path 10a' from the first sub-container 20a' to the downstream sub-connector 19 is filled with the first sub-liquid. Next, the first open/close valve 12a and the variable valve 17 are opened. The first liquid in the first container 20a flows from the first connector 11a into the first flow path 10a. When the first liquid flows past the downstream connector 19 and the mixture injection port 33 and reaches the tip of the needle 31, the first open/close valve 12a and/or the variable valve 17 are closed. A flow path that extends from the first container 20a to the needle 31 through the first flow path 10a and the tube 31 is filled with the first liquid. The above operation to open and close the valves 12a, 12a', 17, and 17' that accompanies the priming operation may be automatically performed by the controller, or may be manually performed by an operator.

Next, the needle 31 is inserted into a patient's vein.

Thereafter, drips of the first liquid to the fifth liquid are sequentially given, similarly to Embodiment 2. In Embodiment 4, however, the second sub-liquid in the second sub-container 20b' needs to be mixed with the second liquid in the second container 20b to give a drip thereof simultaneously with the second liquid. A drip of the first sub-liquid in the first sub-container 20a' needs to be given to the patient before the second sub-liquid. A drip of the third sub-liquid in the third sub-container 20c' needs to be given to the patient after the second sub-liquid. An example of a drip method according to Embodiment 4 will be described, mainly regarding drips of the first to third sub-liquids.

Initially, the controller opens the first open/close valve 12a and the variable valve 17 to start a drip of the first liquid. If the first liquid in the first container 20a runs out, and the second liquid surface sensor 16b detects that the liquid surface has reached the lower limit position, the controller closes the first open/close valve 12a and the variable valve 17.

Next, the controller opens the first sub-open/close valve 12a' and the sub-variable valve 17' to start a drip of the first sub-liquid in the first sub-container 20a'. If the first sub-liquid in the first sub-container 20a' runs out, and the second sub-liquid surface sensor 16b' detects that the liquid surface has reached the lower limit position, the controller closes the first sub-open/close valve 12a' and the sub-variable valve 17'.

Next, the controller opens the second open/close valve 12b and the air discharge tube open/close valve 12g, and also opens the second sub-open/close valve 12b' and the sub-air discharge tube open/close valve 12g'. The second liquid in the second container 20b flows into the second flow path 10b, and the second sub-liquid in the second sub-container 20b' flows into the second sub-flow path 10b'.

As described in Embodiment 2, as a result of the second liquid flowing into the second flow path 10b, air that was in the second flow path 10b prior to the inflow of the second liquid passes through the first branching portion 18a, the first flow path 10a, the drip chamber 14, and the air discharge tube 10g in this order, and is pushed out toward the first container 20a. The second liquid passes through the second flow path 10b, the first branching portion 18a, and the first flow path 10a in this order, and flows into the drip chamber 14. If the first liquid surface sensor 16a detects that the liquid surface has reached the upper limit position, the controller closes the air discharge tube open/close valve 12g. The flow of the second liquid is temporarily stopped.

Similarly, as a result of the second sub-liquid in the second sub-container 20b' flowing into the second sub-flow path 10b', air that was in the second sub-flow path 10b' prior to the inflow of the second sub-liquid passes through the first sub-branching portion 18a', the first sub-flow path 10a', the sub-drip chamber 14', and the sub-air discharge tube 10g' in this order, and is pushed out toward the first sub-container 20a'. The second sub-liquid passes through the second sub-flow path 10b', the first sub-branching portion 18a', and the first sub-flow path 10a' in this order, and flows into the sub-drip chamber 14'. If the first sub-liquid surface sensor 16a' detects that the liquid surface has reached the upper limit position, the controller closes the sub-air discharge tube open/close valve 12g'. The flow of the second sub-liquid is temporarily stopped.

After closing both the air discharge tube open/close valve 12g and the sub-air discharge tube open/close valve 12g', the controller simultaneously opens the variable valve 17 and the sub-variable valve 17. The second liquid moves down the first flow path 10a through the first branching portion 18a, and flows toward the downstream connector 19. Similarly, the second sub-liquid moves down the first sub-flow path 10a' through the first sub-branching portion 18a', and flows toward the downstream sub-connector 19'. The second liquid and the second sub-liquid merge at the mixture injection port 33, and are administered to the patient through the needle 31. The flow rate of the second liquid is monitored by the droplet sensor 15, and is appropriately controlled by adjusting the degree of opening of the variable valve 17. Independently from the monitoring and control of the flow rate of the second liquid, the flow rate of the second sub-liquid is monitored by the sub-droplet sensor 15', and is appropriately controlled by adjusting the degree of opening of the sub-variable valve 17. The liquid surface within the drip chamber 14 is monitored by the first liquid surface sensor 16a and the second liquid surface sensor 16b. Similarly, the liquid surface within the sub-drip chamber 14' is monitored by the first sub-liquid surface sensor 16a' and the second sub-liquid surface sensor 16b'.

If the second liquid in the second container 20b runs out, and the second liquid surface sensor 16b detects that the liquid surface has reached the lower limit position, the controller closes the second open/close valve 12b and the variable valve 17. Similarly, if the second sub-liquid in the second sub-container 20b' runs out, and the second sub-liquid surface sensor 16b' detects that the liquid surface has reached the lower limit position, the controller closes the second sub-open/close valve 12b' and the sub-variable valve 17'.

Next, the controller opens the third sub-open/close valve 12c' and the sub-air discharge tube open/close valve 12g'. The third sub-liquid in the third sub-container 20c' flows into the third sub-flow path 10c'. As a result of the third sub-liquid flowing into the third sub-flow path 10c', air that was in the third sub-flow path 10c' prior to the inflow of the third sub-liquid passes through the first sub-branching portion 18a', the first sub-flow path 10a', the sub-drip chamber 14', and the sub-air discharge tube 10g' in this order, and is pushed out toward the first sub-container 20a'. The third sub-liquid passes through the third sub-flow path 10c', the first sub-branching portion 18a', and the first sub-flow path 10a' in this order, and flows into the sub-drip chamber 14'. If the first sub-liquid surface sensor 16a' detects that the liquid surface has reached the upper limit position, the controller closes the sub-air discharge tube open/close valve 12g'. The flow of the third sub-liquid is temporarily stopped.

Next, the controller opens the sub-variable valve 17'. The third sub-liquid moves down the first sub-flow path 18a' through the first sub-branching portion 10a', and flows toward the downstream sub-connector 19. Thus, the drip of the second sub-liquid remaining in the first sub-flow path 10a' is resumed, and subsequently, a drip of the third sub-liquid is started. The flow rate of the third sub-liquid is monitored by the sub-droplet sensor 15, and is appropriately controlled by adjusting the degree of opening of the sub-variable valve 17'. The liquid surface within the sub-drip chamber 14' is monitored by the first sub-liquid surface sensor 16a' and the second sub-liquid surface sensor 16b'.

If the third sub-liquid in the third sub-container 20b' runs out, and the second sub-liquid surface sensor 16b' detects that the liquid surface has reached the lower limit position, the controller closes the third sub-open/close valve 12c' and the sub-variable valve 17'.

Thereafter, drips of the third liquid to the fifth liquid are sequentially given, similarly to Embodiment 2.

Similarly to Embodiment 3, with the infusion apparatus according to Embodiment 4 as well, drips of two different liquids can be simultaneously given via the shared needle 31, while separately monitoring and independently controlling the flow rates of the two liquids.

The sub-infusion set 2' has the same basic configuration as that of the infusion set 2. Therefore, the sub-infusion set 2' exhibits the following effects, which are similar to those of Embodiment 2.

After a drip of the first sub-liquid has been started, switching between the first sub-container 20a' to the third sub-container 20c' in which the first sub-liquid to the third sub-liquid are stored, and setting of the flow rate of the first sub-liquid to the third sub-liquid are automatically performed. This configuration is advantageous in lightening the work load on an operator and preventing a human error in operation.

The side-injection lines (the second sub-flow path 10b' and the third sub-flow path 10c') are automatically primed after a drip of the first sub-liquid has been started and immediately before drips of the second sub-liquid and third sub-liquid are given, respectively. This configuration is also advantageous in reducing the work load on an operator.

Air that was in the side-injection lines (the second sub-flow path 10b' and the third sub-flow path 10c') before the side-injection lines were primed does not leak out to the outside due to the priming. This configuration is advantageous in reducing the likelihood of medicine exposure due to priming in the case where a hazardous medical solution, such as an anti-cancer agent, is stored in a container that is connected to a side-injection line.

In the configuration in FIG. 4, an upper end of the sub-air discharge tube 10g' is connected to the first sub-flow path 10a' or the first sub-connector 11a', but, for example, the upper end of the sub-air discharge tube 10g' may alternatively be connected to a sealed discharged air collection container (bag) that differs from the first to third sub-containers 20a' to 20c' in which liquids are stored. In this case, air that was in the side-injection lines before priming is collected into the discharged air collection container, rather than the first sub-container 10a'.

In the case where liquids that pose no risk if a person is exposed thereto are stored in the first to third containers 20a' to 20c', the upper end of the sub-air discharge tube 10g' may be open to the outside.

Embodiment 4 is the same as Embodiment 2, except for the above-described configuration. The descriptions of Embodiment 2 are also applied to Embodiment 4.

Embodiments 1 to 4 described above are merely examples. The present invention is not limited to Embodiments 1 to 4 described above, and can be modified as appropriate.

In Embodiments 1 to 4 described above, the second to fifth flow paths (side-injection lines) 10b to 10e are in communication with the first flow path (main line) 10a at the shared first branching portion 18a. In Embodiment 1, this configuration makes is possible to shorten the distance between the first liquid surface sensor 13a and the second liquid surface sensor 13b, and connect all of the second to fifth flow paths 10b to 10e to the first flow path 10a between the first liquid surface sensor 13a and the second liquid surface sensor 13b while bringing the second to fifth flow paths 10b to 10e close to the first liquid surface sensor 13a and the second liquid surface sensor 13b. In Embodiment 1, this configuration is advantageous in facilitating the discharging of air when priming the second to fifth flow paths 10b to 10e and reducing mixing of different liquids when sequentially switching between containers. However, the present invention is not limited thereto. For example, the infusion sets 1 and 2 may have a configuration in which the second to fifth flow paths 10b to 10e do not have a shared flow path portion but are in communication with the first flow path 10a at different branching portions. The same applies to the side-injection lines (the second sub-flow path 10b' and the third sub-flow path 10c') that constitute the sub-infusion sets 1' and 2' according to Embodiments 3 and 4.

The number of side-injection lines included in each infusion set does not need to be four (namely, the second to fifth flow paths 10b to 10e) as in Embodiments 1 to 4 described above, and need only be at least one. The infusion set can exhibit the above-described effects of the present invention if the infusion set includes at least one side-injection line that branches from the main line (the first flow path 10a). Preferably, the number of side-injection lines is two or more. Similarly, the number of side-injection lines included in a sub-infusion set does not need to be two (namely, the second sub-flow path 10b' and the third sub-flow path 10c') as in Embodiments 3 and 4 described above, and need only be at least one. Preferably, the number of side-injection lines is two or more.

In Embodiments 3 and 4, the number of side-injection lines in the infusion set is four, and the number of side-injection lines in the sub-infusion set is two. However, the present invention is not limited thereto. For example, the infusion set and the sub-infusion set may include the same number of side-injection lines. That is to say, the infusion set (main infusion set) and the sub-infusion set may have the same configuration. Since the same infusion set can be used as either the main infusion set or the sub-infusion set, this configuration is advantageous in reducing the number of types of infusion sets and simplifying management and storage of the infusion sets. For example, in Embodiment 3, the same infusion set as the infusion set 1 may be used as the sub-infusion set 1'. In this case, no container is connected to two of the four side-injection lines in the sub-infusion set 1'. The same applies to Embodiment 4.

In Embodiments 3 and 4, a drip of only the second liquid in the second container 20b, out of the first to fifth containers 20a to 20e that are connected to the infusion sets 1 and 2, is given simultaneously with a drip of the second sub-liquid. However, the present invention is not limited thereto. A drip of a liquid in any one or more of the plurality of containers that are connected to the infusion sets 1 and 2 may be given simultaneously with a drip of another liquid, using the sub-infusion sets 1' and 2'. The infusion set (main infusion set) and the sub-infusion set having the same configuration as described above is advantageous in giving drips of two or more of the plurality of liquids, drips of which are sequentially given via the main infusion set, simultaneously with a drip of another liquid.

In Embodiments 3 and 4, the downstream sub-connector 19' in the sub-infusion sets 1' and 2' is connected to the mixture injection port 33 provided on the tube 30, but the configuration for merging a liquid from the infusion sets 1 and 2 with a liquid from the sub-infusion sets 1' and 2' is not limited thereto. For example, a configuration may also be employed in which the mixture injection port 33 is provided at a portion of the first flow path 10a in the infusion sets 1 and 2 between the variable valve 17 and the downstream connector 19, and the downstream sub-connector 19' is connected to this mixture injection port 33. Alternatively, a branch connector that branches to form a "T" shape or a "Y" shape may be used as the connector 32 that is provided at the upstream end of the tube 30 to connect the downstream connector 19 and the downstream sub-connector 19' to this branch connector. Rather than using disconnectable connecting members such as the mixture injection port 33 and the downstream sub-connector 19, a branch tube that branches to form a "T" shape or a "Y" shape may be used, and the downstream end of the first sub-flow path 10a' in the sub-infusion sets 1' and 2' may be connected to one connection opening of the branch tube. This branch tube can be provided at a portion of the first flow path 10a between the variable valve 17 and the downstream connector 19, or on the tube 30.

The infusion apparatus according to the present invention may include one infusion set (main infusion set) and two or more sub-infusion sets. A downstream end of the first sub-flow path 10a' in each of the two or more sub-infusion sets is in communication with a portion of the first flow path 10a on the downstream side of the variable valve 17 or with a flow path (the tube 30) that is connected to the downstream connector 19 in the main infusion set. The two or more sub-infusion sets may have the same configuration, or may have different configurations. Some or all of the two or more sub-infusion sets may have the same configuration as the configuration of the main infusion set, or may have a configuration that differs from the configuration of the main infusion set. By using an infusion apparatus that includes one main infusion set and two or more sub-infusion sets, drips of three of more liquids can be simultaneously given via the shared needle 31 while appropriately controlling the flow rate of these liquids.

The infusion set and the sub-infusion set may further be provided with any other members. For example, the infusion set and the sub-infusion set may be provided with, for example, a filter for filtering a liquid, a mixture injection port for mixing a medical solution or the like with a liquid, or the like.

Figure 5:
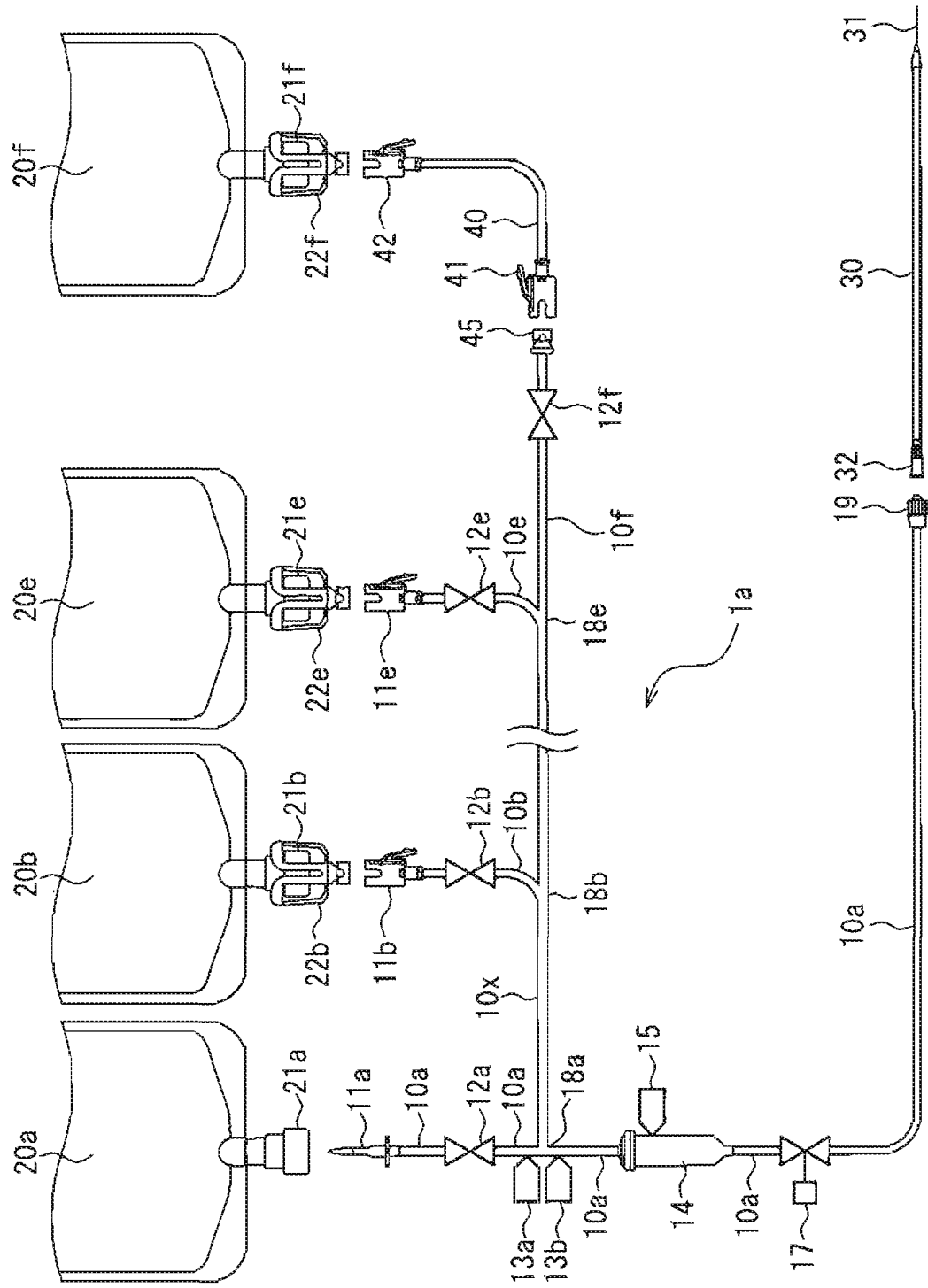
FIG. 5 shows another infusion set according to Embodiment 1 of the present invention in which a side-injection line is provided with a mixture injection port.
Figure 6:
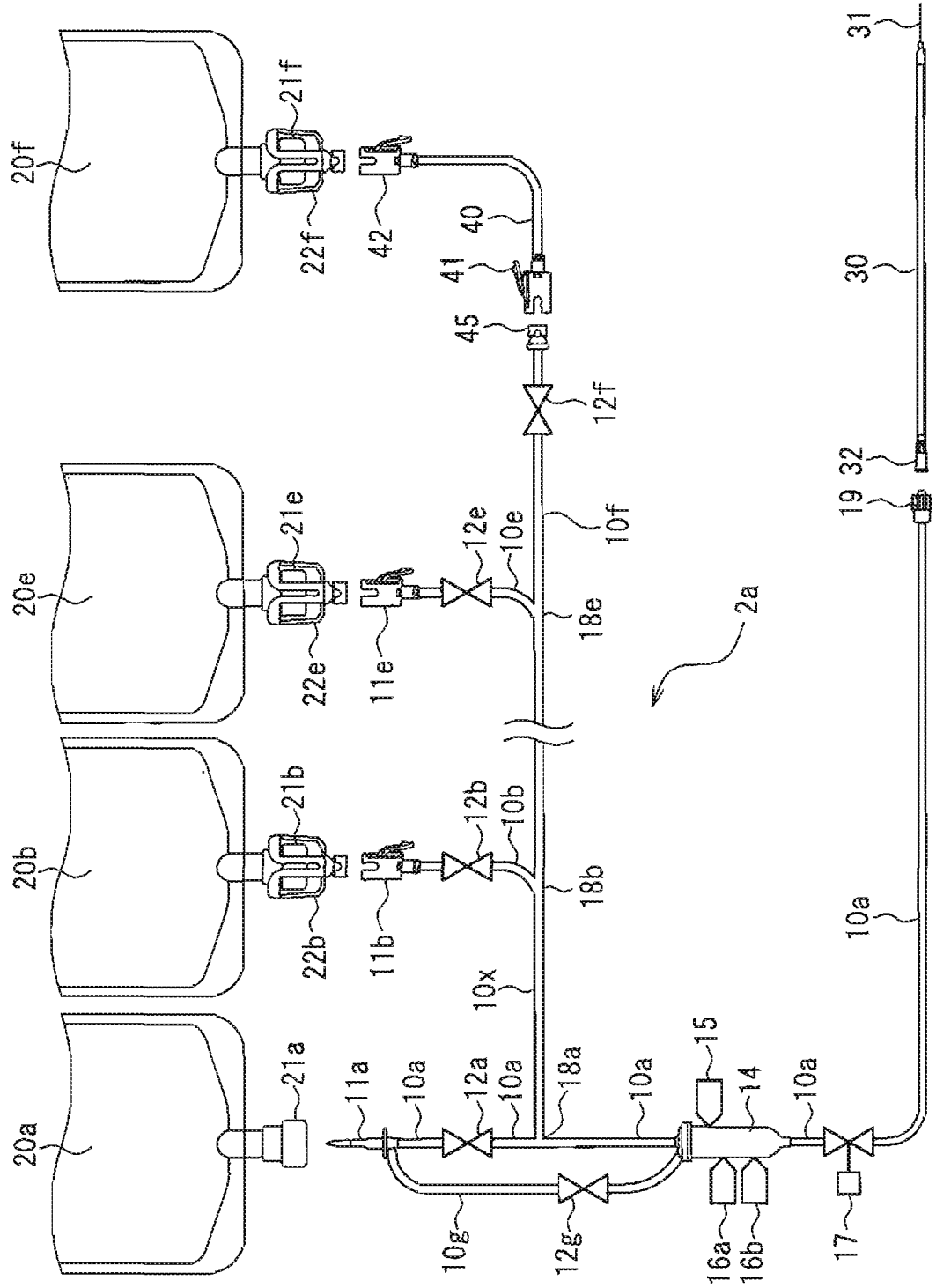
FIG. 6 shows another infusion set according to Embodiment 2 of the present invention in which a side-injection line is provided with a mixture injection port.

FIG. 5 shows an infusion set 1a in which a side-injection line in the infusion set 1 according to Embodiment 1 is provided with a mixture injection port 45. FIG. 6 shows an infusion set 2a in which a side-injection line in the infusion set 2 according to Embodiment 2 is provided with the mixture injection port 45. FIGS. 5 and 6 omit the third container 20c, the fourth container 20d, and members associated with these containers to simplify the drawings. As shown in FIGS. 5 and 6, a fifth branching portion 18e, which has a T shape (or a Y shape), is provided on the branch flow path 10x, and the fifth flow path 10e and a sixth flow path 10f branch from the fifth branching portion 18e. A sixth open/close valve 12f is provided on the sixth flow path 10f, and the mixture injection port 45 is provided at a terminal of the sixth flow path 10f. The sixth open/close valve 12f is an electric pinch clamp, for example, similarly to the first to fifth open/close valve 12a to 12e, and is opened and closed based on a signal from the controller (not shown). Although the configuration of the mixture injection port 45 is not limited, the mixture injection port 45 may be constituted by a female connector (e.g. see Patent Document 7) that has an elastic partition member called a septum. The sixth container 20f can be connected to the mixture injection port 45 via an extension tube 40. A connector 41, which is to be connected to the mixture injection port 45, is provided at one end of the extension tube 40, and a connector 42, which is to be connected to a port 21f of the sixth container 20f via an adapter 22lf is provided at the other end of the extension tube 40. Although the connectors 41 and 42 are not limited, they may be lever lock connectors that are the same as the second to fifth connectors 11b to 11e. The sixth container 20f may have the same configuration as the configuration of the first to fifth containers 20a to 20e, and the adapter 22f may have the same configuration as the configuration of the adapters 22b to 22e. The mixture injection port 45 with which a side-injection line is provided has substantially the same effects as the effects achieved in the case of increasing the number of side-injection lines in the infusion set. A liquid in the sixth container 20f can be administered to a patient via the mixture injection port 45 similarly to Embodiments 1 and 2, when needed. By making the connector 42 different from the second to fifth connectors 11b to 11e, a container with a port to which the second to fifth connectors 11b to 11e cannot be connected can be connected to the infusion set via the mixture injection port 45. In FIGS. 5 and 6, the sixth open/close valve 12f may alternatively be provided on the extension tube 40, rather than on the sixth flow path 10f. A side-injection line in the infusion sets 1' and 2' according to Embodiments 3 and 4 may also be provided with the mixture injection port 45.

The configuration of the connectors to be connected to a container for storing liquids is not limited to puncture needles (the first connector 11a, the first sub-connector 11a') and lever lock connectors (the second to fifth connectors 11b to 11e, the second and third sub-connectors 11b' and 11c'), and may be any other configuration. All of the connectors may have the same configuration, or some of the connectors may have a different configuration. The connector provided in the main line may be the same as the connectors that are provided in the side-injection lines.

The containers that are connected to the infusion set and the sub-infusion set may have any configuration. The containers may be infusion bags formed by adhering soft sheets, or may be bottles that are made of a hard material and are not substantially deformed. The ports of the containers are not limited to those sealed with rubber plugs. The configuration of the adapters that are interposed between the ports and the connectors in the infusion set is not limited to those described in the above-described embodiments either, and may also be any other configuration. The connectors may be directly connected to the ports without using the adapters.

Any type of liquid may be administered using the infusion apparatus according to the present invention. A medical solution that contains a hazardous medicine, such as an anti-cancer agent, may be administered, or a liquid that contains a nutrient, an electrolyte, or the like and poses no risk if a person is exposed thereto may be administered.

INDUSTRIAL APPLICABILITY

The infusion apparatus according to the present invention can be favorably used in the medical field in the case of administering a plurality of types of liquids to a patient. In particular, the infusion apparatus according to the present invention is preferable in the case of administering a hazardous medical solution, such as an anti-cancer agent, to which an operator may be exposed.

DESCRIPTION OF REFERENCE NUMERALS 1, 2 Infusion set
1', 2' Sub-infusion set
10a to 10e Flow path
10a' to 10c' Sub-flow path
10g Air discharge tube
10g' Sub-air discharge tube
11a to 11e Connector
11a' to 11c' Sub-connector
12a to 12e Open/close valve
12a' to 12c' Sub-open/close valve
12g Air discharge tube open/close valve
12g' Sub-air discharge tube open/close valve
13a First liquid surface sensor
13a' First sub-liquid surface sensor
13b Second liquid surface sensor
13b' Second sub-liquid surface sensor
14 Drip chamber
14' Sub-drip chamber
15 Droplet sensor
15' Sub-droplet sensor
16a First liquid surface sensor
16a' First sub-liquid surface sensor
16b Second liquid surface sensor
16b' Second sub-liquid surface sensor
17 Variable valve
17' Sub-variable valve
19 Downstream connector
19' Downstream sub-connector
20a to 20e Container
20a' to 20c' Sub-container

The invention claimed is:

1. An infusion apparatus comprising:
an infusion set; and
a controller,
the infusion set including:
 a first flow path having a first connector, which is to be connected to a first container for storing a first liquid, at one end, and a downstream connector at the other end;
 a first open/close valve, a first liquid surface sensor, a second liquid surface sensor, a drip chamber, and a variable valve that are provided in this order on the first flow path from the first connector end toward the downstream connector end;
 a droplet sensor that the drip chamber is provided with;
 a second flow path having a second connector, which is to be connected to a second container for storing a second liquid, at one end; and
 a second open/close valve provided on the second flow path,
 wherein the second flow path is in communication with a portion of the first flow path between the first liquid surface sensor and the second liquid surface sensor, and
 the controller is configured to control the first open/close valve, the variable valve, and the second open/close valve based on signals from the first liquid surface sensor, the second liquid surface sensor, and the droplet sensor.

2. The infusion apparatus according to claim 1,
wherein, if the second liquid surface sensor detects an interface between the first liquid and air, in a state where the second open/close valve is closed and the first open/close valve and the variable valve are opened to flow the first liquid from the first container toward the downstream connector, the variable valve is closed and the second open/close valve is opened to flow the second liquid into the second flow path, and if the first liquid surface sensor detects an interface between air and the second liquid, the first open/close valve is closed and the variable valve is opened to flow the second liquid from the second container toward the downstream connector.

3. The infusion apparatus according to claim 1,
wherein the infusion set further includes:
- a third flow path having a third connector, which is to be connected to a third container for storing a third liquid, at one end; and
- a third open/close valve provided on the third flow path, wherein the third flow path is in communication with a portion of the first flow path between the first liquid surface sensor and the second liquid surface sensor, and the controller is configured to control the third open/close valve based on a signal from the second liquid surface sensor.

4. The infusion apparatus according to claim 3,
wherein, if the second liquid surface sensor detects an interface between the second liquid and air, in a state where the first open/close valve and the third open/close valve are closed and the second open/close valve and the variable valve are opened to flow the second liquid from the second container toward the downstream connector, the second open/close valve and the variable valve are closed and the first open/close valve and the third open/close valve are opened to flow the third liquid into the third flow path, and if the first liquid surface sensor detects an interface between air and the third liquid, the first open/close valve is closed and the variable valve is opened to flow the third liquid from the third container toward the downstream connector.

5. The infusion apparatus according to claim 1, further comprising:
a sub-infusion set including:
- a first sub-flow path having a first sub-connector, which is to be connected to a first sub-container for storing a first sub-liquid, at one end, the other end being configured to be in communication with a portion of the first flow path on the downstream connector end of the variable valve, or with a flow path that is to be connected to the downstream connector in the infusion set;
- a first sub-open/close valve, a first sub-liquid surface sensor, a second sub-liquid surface sensor, a sub-drip chamber, and a sub-variable valve that are provided in this order on the first sub-flow path from the first sub-connector end toward the other end of the first sub-flow path;
- a sub-droplet sensor that the sub-drip chamber is provided with;
- a second sub-flow path having a second sub-connector, which is to be connected to a second sub-container for storing a second sub-liquid, at one end; and
- a second sub-open/close valve provided on the second sub-flow path, wherein the second sub-flow path is in communication with a portion of the first sub-flow path between the first sub-liquid surface sensor and the second sub-liquid surface sensor, and the controller is configured to control the first sub-open/close valve, the sub-variable valve, and the second sub-open/close valve based on signals from the first sub-liquid surface sensor, the second sub-liquid surface sensor, and the sub-droplet sensor.

6. The infusion apparatus according to claim 5,
wherein the variable valve in the infusion set and the sub-variable valve in the sub-infusion set are configured to open simultaneously.

7. An infusion apparatus comprising:
an infusion set; and
a controller,
the infusion set including:
- a first flow path having a first connector, which is to be connected to a first container for storing a first liquid, at one end, and a downstream connector at the other end;
- a first open/close valve, a drip chamber, and a variable valve that are provided in this order on the first flow path from the first connector end toward the downstream connector end;
- a droplet sensor, a first liquid surface sensor, and a second liquid surface sensor that the drip chamber is provided with in this order from an upper end toward a lower end;
- an air discharge tube that is in communication with a gas storing portion in the drip chamber;
- an air discharge tube open/close valve that the air discharge tube is provided with;
- a second flow path having a second connector, which is to be connected to a second container for storing a second liquid, at one end; and
- a second open/close valve provided on the second flow path, wherein the second flow path is in communication with a portion of the first flow path between the first open/close valve and the drip chamber, and the controller is configured to control the first open/close valve, the variable valve, the second open/close valve, and the air discharge tube open/close valve based on signals from the droplet sensor, the first liquid surface sensor, and the second liquid surface sensor.

8. The infusion apparatus according to claim 7, wherein the air discharge tube is in communication with a portion of the first flow path on the first connector end of the first open/close valve, or with the first connector.

9. The infusion apparatus according to claim 7,
wherein, if the second liquid surface sensor detects that a liquid surface within the drip chamber has reached a lower limit position, in a state where the second open/close valve and the air discharge tube open/close valve are closed and the first open/close valve and the variable valve are opened to flow the first liquid from the first container toward the downstream connector, the first open/close valve and the variable valve are closed and the second open/close valve and the air discharge tube open/close valve are opened to flow the second liquid into the second flow path, and if the first liquid surface sensor detects that the liquid surface within the drip chamber has reached an upper limit position, the air discharge tube open/close valve is closed and the variable valve is opened to flow the second liquid from the second container toward the downstream connector.

10. The infusion apparatus according to claim 7,
wherein the infusion set further includes:
   a third flow path having a third connector, which is to be connected to a third container for storing a third liquid, at one end; and
   a third open/close valve provided on the third flow path,
the third flow path is in communication with a portion of the first flow path between the first open/close valve and the drip chamber, and
the controller is configured to control the third open/close valve based on a signal from the second liquid surface sensor.

11. The infusion apparatus according to claim 10,
wherein, if the second liquid surface sensor detects that a liquid surface within the drip chamber has reached a lower limit position, in a state where the first open/close valve, the third open/close valve, and the air discharge tube open/close valve are closed and the second open/close valve and the variable valve are opened to flow the second liquid from the second container toward the downstream connector, the second open/close valve and the variable valve are closed and the third open/close valve and the air discharge tube open/close valve are opened to flow the third liquid into the third flow path, and
if the first liquid surface sensor detects that the liquid surface within the drip chamber has reached an upper limit position, the air discharge tube open/close valve is closed and the variable valve is opened to flow the third liquid from the third container toward the downstream connector.

12. The infusion apparatus according to claim 7, further comprising:
   a sub-infusion set including:
      a first sub-flow path having a first sub-connector, which is to be connected to a first sub-container for storing a first sub-liquid, at one end, the other end being configured to be in communication with a portion of the first flow path on the downstream connector end of the variable valve, or with a flow path that is to be connected to the downstream connector in the infusion set;
      a first sub-open/close valve, a sub-drip chamber, and a sub-variable valve that are provided in this order on the first sub-flow path from the first sub-connector end toward the other end of the first sub-flow path;
      a sub-droplet sensor, a first sub-liquid surface sensor, and a second sub-liquid surface sensor that the sub-drip chamber is provided with in this order from an upper end toward a lower end;
      a sub-air discharge tube that is in communication with a gas storing portion in the sub-drip chamber;
      a sub-air discharge tube open/close valve that the sub-air discharge tube is provided with;
      a second sub-flow path having a second sub-connector, which is to be connected to a second sub-container for storing a second sub-liquid, at one end; and
      a second sub-open/close valve provided on the second sub-flow path, wherein the second sub-flow path is in communication with a portion of the first sub-flow path between the first sub-open/close valve and the sub-drip chamber, and
   the controller is configured to control the first sub-open/close valve, the sub-variable valve, the second sub-open/close valve, and the sub-air discharge tube open/close valve based on signals from the sub-droplet sensor, the first sub-liquid surface sensor, and the second sub-liquid surface sensor.

13. The infusion apparatus according to claim 12,
wherein the variable valve in the infusion set and the sub-variable valve in the sub-infusion set are configured to open simultaneously.

* * * * *